(12) United States Patent
Kanamori et al.

(10) Patent No.: US 9,309,312 B2
(45) Date of Patent: Apr. 12, 2016

(54) IMMUNOASSAY METHOD FOR HUMAN CXCL1 PROTEIN

(75) Inventors: Satoko Kanamori, Kanagawa (JP); Giman Jung, Kanagawa (JP); Yoshinori Tanaka, Kanagawa (JP); Aiko Takayama, Kanagawa (JP)

(73) Assignee: TORAY INDUSTRIES, INC., Tokyo (JP)

(*) Notice: Subject to any disclaimer, the term of this patent is extended or adjusted under 35 U.S.C. 154(b) by 382 days.

(21) Appl. No.: 13/126,877

(22) PCT Filed: Oct. 29, 2009

(86) PCT No.: PCT/JP2009/068587
§ 371 (c)(1),
(2), (4) Date: Apr. 29, 2011

(87) PCT Pub. No.: WO2010/050554
PCT Pub. Date: May 6, 2010

(65) Prior Publication Data
US 2011/0287444 A1    Nov. 24, 2011

(30) Foreign Application Priority Data

Oct. 31, 2008 (JP) .................................. 2008-281908
Feb. 23, 2009 (JP) .................................. 2009-039411

(51) Int. Cl.
| C07K 16/24 | (2006.01) |
| G01N 33/68 | (2006.01) |
| G01N 33/543 | (2006.01) |
| G01N 33/563 | (2006.01) |
| A61K 39/00 | (2006.01) |

(52) U.S. Cl.
CPC .............. *C07K 16/24* (2013.01); *G01N 33/543* (2013.01); *G01N 33/6857* (2013.01); *G01N 33/6863* (2013.01); *A61K 2039/505* (2013.01); *C07K 2317/34* (2013.01); *C07K 2317/565* (2013.01); *C07K 2317/76* (2013.01); *G01N 2333/522* (2013.01)

(58) Field of Classification Search
CPC .............. C07K 16/24; C07K 2317/34; C07K 2317/565; C07K 2317/76; G01N 33/543; G01N 33/6857; G01N 33/6863; G01N 2333/522; A61K 2039/505
USPC .......... 435/7.1, 7.23, 7.94, 40.52, 70.21, 452, 435/331, 335, 344.1; 436/503, 512, 518, 436/536, 548, 815; 530/387.9, 388.23, 530/388.85, 389.2, 391.1, 391.3
See application file for complete search history.

(56) References Cited

U.S. PATENT DOCUMENTS

| 5,501,969 | A  | * | 3/1996  | Hastings et al. ......... 435/252.33 |
| 7,504,225 | B2 | * | 3/2009  | Ring et al. .................. 435/7.1 |
| 7,598,028 | B2 | * | 10/2009 | Macoska ....................... 435/4 |
| 7,910,316 | B2 | * | 3/2011  | Akiyama et al. ............... 435/7.1 |
| 7,919,083 | B2 | * | 4/2011  | Lillard et al. ............... 424/130.1 |
| 2008/0206766 | A1 |  | 8/2008  | Macoska |
| 2009/0203039 | A1 |  | 8/2009  | Kominami et al. |

FOREIGN PATENT DOCUMENTS

| CA | 2621060 A1 | 3/2007 |
| CN | 101290318 A | 10/2008 |
| EP | 1930445 A1 | 6/2008 |
| WO | WO 2007/026895 A1 | 3/2007 |
| WO | WO 2008/013257 A1 | 1/2008 |

OTHER PUBLICATIONS

Hellström et al., 1985. In Monoclonal Antibodies for Cancer Detection and Therapy (Baldwin et al, eds.), Academic Press, London. p. 20.*
Tekamp-Olson et al., 1990. Cloning and characterization of cDNAs for murine macrophage inflammatory protein 2 and its human homologues. J. Exp. Med. 172: 911-919.*
International Search Report dated Nov. 24, 2009 for PCT/JP2009/068587.
Kawanishi et al., "Secreted CXCL1 Is a Potential Mediator and Marker of the Tumor Invasion of Bladder Cancer", Human Cancer Biology, Clin Cancer Res, May 1, 2008, vol. 14, No. 9, pp. 2579-2587.
Wen et al., "GROα Is Highly Expressed in Adenocarcinoma of the Colon and Down-Regulates Fibulin-1", Human Cancer Biology, Clin Cancer Res, Oct. 15, 2006, vol. 12, No. 20, pp. 5951-5959.
Yang et al., "The chemokine growth-regulated oncogene 1 (Gro-1) links RAS signaling to the senescence of stromal fibroblasts and ovarian tumorigenesis", Proc. Natl. Acad, Sci, USA, Oct. 31, 2006, vol. 103, No. 44, pp. 16472-16477.

(Continued)

*Primary Examiner* — Gail R Gabel
*Assistant Examiner* — James L Grun
(74) *Attorney, Agent, or Firm* — Birch, Stewart, Kolasch & Birch, LLP

(57) ABSTRACT

An object of the present invention is to detect a human CXCL1 protein with high sensitivity. An immunoassay method is provided for a human CXCL1 protein, by which human CXCL1 or a fragment thereof in a sample is measured using two or more types of anti-human CXCL1 monoclonal antibodies or fragments thereof, wherein:
  each of the two or more types of anti-human CXCL1 monoclonal antibodies or fragments thereof specifically recognizes any one of sequence regions of the amino acid sequences shown in SEQ ID NOS: 1-3, which are partial sequences of the amino acid sequence composing a human CXCL1 protein; and
  the two or more types of anti-human CXCL1 monoclonal antibodies or fragments thereof specifically recognize sequence regions that differ from each other.
Monoclonal antibodies or fragments thereof are provided, each of which specifically recognizes any one sequence region of the amino acid sequences shown in SEQ ID NOS: 1-3 and has a new amino acid sequence.

15 Claims, 9 Drawing Sheets

(56) References Cited

OTHER PUBLICATIONS

Fontana et al., "Probing protein structure by limited proteolysis", Acta Biochimica Polonica, vol. 51, No. 2 (2004) pp. 299-321.

Kennett et al., "Monoclonal antibodies, Hybridomas: A new dimension of biological analysis", Plenum Press, New York, 1980, pp. 1-5.

Russian Office Action issued in Russian Patent Application No. 2011121818 on Jun. 21, 2013.

Sveshnikov et al., "The Introduction to Molecular immunology and Hybridoma Technology", Moscow University Press, Moscow, 2006, pp. 6-8.

Extended European Search Report issued in European Patent Application No. 09823664.9 on Oct. 1, 2013.

Canadian Office Action for Application No. 2,742,157 dated Jul. 8, 2015.

* cited by examiner

─☐─ Immobilized IgG2b-1 x Labeled IgG1-10 (0.6 μg/mL)

─△─ Immobilized IgG2b-1 x Labeled IgG1-10 (0.3 μg/mL) + IgG1-14 (0.3 μg/mL)

Enlarged view of a low-concentration range in the above graph.

- ● (Example 10) Immobilized commercial monoclonal antibody produced by R&D SYSTEMS x Labeled IgG1-10
- □ (Comparative example 1) Commercial kit produced by R&D SYSTEMS.

Enlarged view of a low-concentration range in the above graph.

IMMUNOASSAY METHOD FOR HUMAN CXCL1 PROTEIN

TECHNICAL FIELD

The present invention relates to a method for measuring a human CXCL1 protein (hereinafter, referred to as CXCL1). More specifically, the present invention relates to an immunoassay method that is a method for measuring human CXCL1 using a combination of monoclonal antibodies or fragments thereof each specifically binding to a partial sequence region at any one of three specific positions on the amino acid sequence composing human CXCL1. Also, the present invention relates to monoclonal antibodies or fragments thereof specifically binding to human CXCL1, which can be used for the above method for measuring a human CXCL1 protein.

BACKGROUND ART

Human CXCL1 is a kind of chemokine belonging to the CXC family. In blood, this protein is present in blood platelets and is known to be over-expressed upon inflammation reactions in a manner similar to that of other members of the CXC family.

In recent years, it has been reported that human CXCL1 functions as a tumor-related factor. Therefore, it is expected that human CXCL1 can serve as a urothelial cancer marker through quantitative detection of human CXCL1 in urine (Hiroaki Kawanishi et al, 2008, Clinical Cancer Research, vol. 14, No. 9, 2579-2587; and WO2007/026895). It has been further reported that the amount of human CXCL1 fluctuates at the gene level and at the protein level in the tissue or blood of patients with other malignant tumors such as large-bowel cancer, ovary cancer, or malignant melanoma (Gong Yang et al, 2006, PNAS, vol. 103, No. 44, 16472-16477; Yu Wen et al, 2006, Clinical Cancer Research, vol. 12, No. 20, 5951-5959; and Jing Luan et al, 1997, Journal of Leukocyte Biology, vol. 62, No. 5, 588-597). The human CXCL1 potentially enables extremely early and/or early detection of such cancers, in addition to urothelial cancer.

However, measurement methods using an existing enzyme immunoassay have insufficient sensitivity for detection of the above cancers. For example, WO2007/026895 discloses a kit for measuring human CXCL1 produced by R&D SYSTEMS, Inc. (hereinafter, R&D SYSTEMS), wherein, although the detection limit concentration is around 20 pg/mL, the concentration of human CXCL1 in the urine of a healthy subject does not reach the detection limit. Hence, a method for measuring human CXCL1 with higher sensitivity has been desired.

DISCLOSURE OF THE INVENTION

In an embodiment of the present invention, an object of the present invention is thus to provide an immunoassay method for detecting human CXCL1 with higher sensitivity. More specifically, an object of the present invention is to realize a method for detecting human CXCL1 with higher sensitivity by an immunoassay using a combination of antibodies or antigen recognition regions each specifically binding to a sequence at any one of 3 specific positions in the amino acid sequence composing human CXCL1.

Also, in another embodiment of the present invention, an object of the present invention is to provide monoclonal antibodies or fragments thereof specifically recognizing human CXCL1. More specifically, another object of the present invention is to provide monoclonal antibodies or fragments thereof that can be used for the above method for detecting human CXCL1 with higher sensitivity, comprise new amino acid sequences specifically recognizing human CXCL1, and have affinity for human CXCL1 higher than that of conventional antibodies.

Means to Solve the Problems

As a result of intensive studies to achieve the above objects, the present inventors have discovered that human CXCL1 can be detected with higher sensitivity than conventional methods by immunological determination using a combination of monoclonal antibodies or antigen recognition portions specifically binding to partial sequence regions at 3 specific positions in the amino acid sequence composing human CXCL1. Also, the present inventors have succeeded in preparation of monoclonal antibodies comprising new amino acid sequences specifically binding to partial sequences at the 3 positions on the above human CXCL1 and hybridomas producing such antibodies. Moreover, the present inventors have isolated genes encoding the amino acid sequences composing the antibodies and determined the nucleotide sequences. This has made it possible to prepare recombinant antibodies and recombinant fragments thereof. The present invention has been achieved based on the above findings in order to provide the following (1) to (15).

(1) An immunoassay method for a human CXCL1 protein, by which human CXCL1 or a fragment thereof in a sample is measured using two or more types of anti-human CXCL1 monoclonal antibodies or fragments thereof, wherein:

the two or more types of anti-human CXCL1 monoclonal antibodies or fragments thereof specifically recognize any one of the sequence regions of the amino acid sequences shown in SEQ ID NOS: 1-3 that are partial sequences of the amino acid sequence composing the human CXCL1 protein; and the two or more types of anti-human CXCL1 monoclonal antibodies or fragments thereof specifically recognize sequence regions that differ from each other.

(2) The immunoassay method for a human CXCL1 protein according to (1), by which a human CXCL1 protein or a fragment thereof in a sample is measured using an anti-human CXCL1 monoclonal antibody or a fragment thereof that specifically recognizes the amino acid sequence region shown in SEQ ID NO: 3.

(3) The immunoassay method for a human CXCL1 protein according to (1) or (2), by which a human CXCL1 protein or a fragment thereof in a sample is measured using an anti-human CXCL1 monoclonal antibody or a fragment thereof that specifically recognizes the amino acid sequence region shown in SEQ ID NO: 1 and an anti-human CXCL1 monoclonal antibody or a fragment thereof that specifically recognizes the amino acid sequence region shown in SEQ ID NO: 3.

(4) The immunoassay method for a human CXCL1 protein according to (1) or (2), by which a human CXCL1 protein or a fragment thereof in a sample is measured using an anti-human CXCL1 monoclonal antibody or a fragment thereof that specifically recognizes the amino acid sequence region shown in SEQ ID NO: 2 and an anti-human CXCL1 monoclonal antibody or a fragment thereof that specifically recognizes the amino acid sequence region shown in SEQ ID NO: 3.

(5) The immunoassay method for a human CXCL1 protein according to any one of (1) to (4), wherein the sample is a tissue collected after an operation, blood, serum, blood plasma, urine, spinal fluid, saliva, lymph fluid, lacrimal fluid, or seminal fluid.

(6) An anti-human CXCL1 monoclonal antibody or a fragment thereof, which specifically recognizes the partial sequence shown in SEQ ID NO: 3 in the amino acid sequence composing the human CXCL1 protein, wherein:

in its light chains, CDR1 comprises the amino acid sequence shown in SEQ ID NO: 4, CDR2 comprises the amino acid sequence shown in SEQ ID NO: 5, and CDR3 comprises the amino acid sequence shown in SEQ ID NO: 6;

in its heavy chains, CDR1 comprises the amino acid sequence shown in SEQ ID NO: 7, CDR2 comprises the amino acid sequence shown in SEQ ID NO: 8, and CDR3 comprises the amino acid sequence shown in SEQ ID NO: 9.

(7) The anti-human CXCL1 monoclonal antibody or a fragment thereof according to (6), containing the amino acid sequence shown in SEQ ID NO: 10 in a light-chain variable region and the amino acid sequence shown in SEQ ID NO: 11 in a heavy-chain variable region.

(8) An anti-human CXCL1 monoclonal antibody or a fragment thereof, which specifically recognizes the partial sequence shown in SEQ ID NO: 1 in the amino acid sequence composing a human CXCL1 protein, wherein:

in its light chains, CDR1 comprises the amino acid sequence shown in SEQ ID NO: 12, CDR2 comprises the amino acid sequence shown in SEQ ID NO: 13, and CDR3 comprises the amino acid sequence shown in SEQ ID NO: 14; and in its heavy chains, CDR1 comprises the amino acid sequence shown in SEQ ID NO: 15, CDR2 comprises the amino acid sequence shown in SEQ ID NO: 16, and CDR3 comprises the amino acid sequence shown in SEQ ID NO: 17.

(9) The anti-human CXCL1 monoclonal antibody or a fragment thereof according to (8), containing the amino acid sequence shown in SEQ ID NO: 18 in a light-chain variable region and the amino acid sequence shown in SEQ ID NO: 19 in a heavy-chain variable region.

(10) An anti-human CXCL1 monoclonal antibody or a fragment thereof, which that specifically recognizes the partial sequence shown in SEQ ID NO: 3 in the amino acid sequence composing a human CXCL1 protein, wherein:

in its light chains, CDR1 comprises the amino acid sequence shown in SEQ ID NO: 20, CDR2 comprises the amino acid sequence shown in SEQ ID NO: 21, and CDR3 comprises the amino acid sequence shown in SEQ ID NO: 22; and in its heavy chains, CDR1 comprises the amino acid sequence shown in SEQ ID NO: 23, CDR2 comprises the amino acid sequence shown in SEQ ID NO: 24, and CDR3 comprises the amino acid sequence shown in SEQ ID NO: 25.

(11) The anti-human CXCL1 monoclonal antibody or a fragment thereof according to (10), containing the amino acid sequence shown in SEQ ID NO: 26 in a light-chain variable region and the amino acid sequence shown in SEQ ID NO: 27 in a heavy-chain variable region.

(12) An anti-human CXCL1 monoclonal antibody or a fragment thereof, which is a monoclonal antibody or a fragment thereof that specifically recognizes the partial sequence shown in SEQ ID NO: 2 in the amino acid sequence composing a human CXCL1 protein, wherein:

in its light chains, CDR1 comprises the amino acid sequence shown in SEQ ID NO: 28, CDR2 comprises the amino acid sequence shown in SEQ ID NO: 29, and CDR3 comprises the amino acid sequence shown in SEQ ID NO: 30; and in its heavy chains, CDR1 comprises the amino acid sequence shown in SEQ ID NO: 31, CDR2 comprises the amino acid sequence shown in SEQ ID NO: 32, and CDR3 comprises the amino acid sequence shown in SEQ ID NO: 33.

(13) The anti-human CXCL1 monoclonal antibody or a fragment thereof according to (12), containing the amino acid sequence shown in SEQ ID NO: 34 in a light-chain variable region and the amino acid sequence shown in SEQ ID NO: 35 in a heavy-chain variable region.

(14) An anti-human CXCL1 monoclonal antibody or a fragment thereof, which is a monoclonal antibody or a fragment thereof that specifically recognizes the partial sequence shown in SEQ ID NO: 3 in the amino acid sequence composing a human CXCL1 protein, wherein:

in its light chains, CDR1 comprises the amino acid sequence shown in SEQ ID NO: 36, CDR2 comprises the amino acid sequence shown in SEQ ID NO: 37, and CDR3 comprises the amino acid sequence shown in SEQ ID NO: 38; and in its heavy chains, CDR1 comprises the amino acid sequence shown in SEQ ID NO: 39, CDR2 comprises the amino acid sequence shown in SEQ ID NO: 40, and CDR3 comprises the amino acid sequence shown in SEQ ID NO: 41.

(15) The anti-human CXCL1 monoclonal antibody or a fragment thereof according to (14), containing the amino acid sequence shown in SEQ ID NO: 42 in a light-chain variable region and the amino acid sequence shown in SEQ ID NO: 43 in a heavy-chain variable region.

Effect of the Invention

According to the present invention, the concentration of human CXCL1 can be measured with higher sensitivity than conventional methods. Also, a high-affinity anti-human CXCL1 monoclonal antibody or a fragment thereof specifically recognizing human CXCL1 can be provided.

MODE OF CARRYING OUT THE INVENTION

Figure 1:
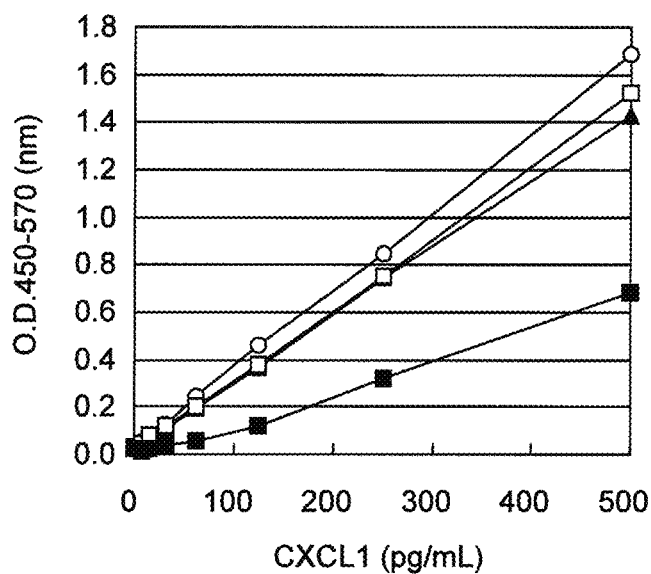
FIG. 1 shows immunoassay according to a conventional method using a sandwich ELISA method using a monoclonal antibody that specifically recognizes any one of the amino acid sequences shown in SEQ ID NOS: 1-3 and a commercial kit.
Figure 1:
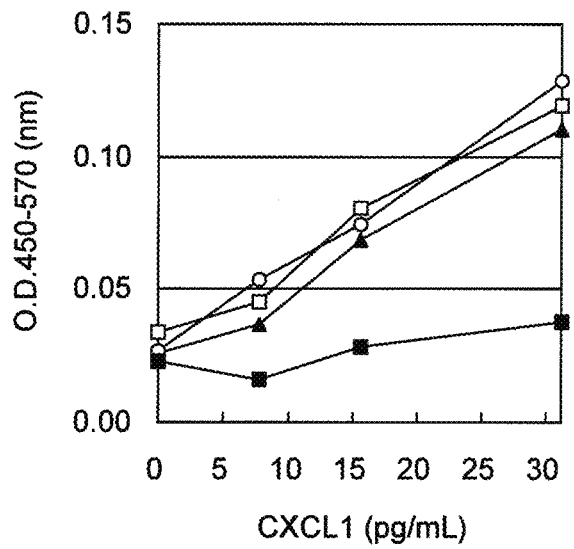

Embodiments of the invention will be hereafter described in detail.

1. Anti-Human CXCL1 Monoclonal Antibody and a Fragment Thereof.

The term "human CXCL1" as used herein refers to a protein or a natural mutant thereof comprising the amino acid sequence according to Genbank NM_001511. The term "natural mutant" refers to a mutant existing in the nature. Examples of such a mutant include a mutant comprising an amino acid sequence having a deletion, a substitution, an addition, or an insertion of one or several amino acids in the aforementioned amino acid sequence of human CXCL1 and a mutant having 95% or more, preferably 98% or more, and more preferably 99% or more amino acid sequence identity with the aforementioned amino acid sequence of human CXCL1. Here, the term "identity" refers to the percentage (%) of the total number of amino acid residues of the amino acid sequence in question that are identical to amino acid residues of the amino acid sequence of human CXCL1 when the two amino acid sequences are aligned such that the highest possible degree of agreement between them is achieved. In this case, sequence alignment can be carried out by introducing or not introducing gaps, and the number of gaps introduced is included when the percentage is calculated. Also, the term "several" refers to an integer between 2 and 10, such as between 2 and 7, 2 and 5, 2 and 4, and 2 and 3. Specific examples of a natural mutant include mutants based on polymorphism such as SNP (single nucleotide polymorphism) and splicing mutants. The above substitution is preferably a conservative amino acid substitution. If the substitution is a conservative amino acid substitution, a mutant resulting from the conservative amino acid substitution may have a structure or properties substantially equivalent to those of human CXCL1 having the above amino acid sequence. As conservative amino acids, nonpolar amino acids (glycine, alanine, phenylalanine, valine, leucine, isoleucine, methionine, proline, and tryptophan) and polar amino acids (amino acids other than nonpolar amino acids), charged amino acids (acidic amino acids (aspartic acid and glutamic acid) and basic amino acids (arginine, histidine, and lysine)) and non-charged amino acids (amino acids other than charged amino acids), aromatic amino acids (phenylalanine, tryptophan, and tyrosine), branched amino acids (leucine, isoleucine, and valine), and aliphatic amino acids (glycine, alanine, leucine, isoleucine, and valine), are known, for example.

The term "monoclonal antibody" as used herein refers to a polypeptide containing an immunoglobulin- or its fragment-derived framework region (FR) and a complementary determining region (CDR) and being capable of specifically binding to and recognizing an antigen. Therefore, the term "anti-human CXCL1 monoclonal antibody" in the present invention refers to a polypeptide capable of specifically binding to human CXCL1 or a fragment thereof and recognizing the human CXCL1 or a fragment thereof. The term "specifically binding" refers to binding to only a target antigen (human CXCL1 or a fragment thereof in the present invention).

A typical immunoglobulin molecule consists of a tetramer in which two sets, each consisting of two polypeptide chains referred to as a heavy chain and a light chain, are connected to each other via disulfide bond. A heavy chain comprises a heavy chain variable region ($V_H$) on the N-terminus and a heavy chain constant region ($C_H$) on the C-terminus. A light chain comprises a light chain variable region ($V_L$) on the N-terminus and a light chain constant region ($C_L$) on the C-terminus. Of these regions, $V_H$ and $V_L$ are particularly important since they are involved in the binding specificity of the antibody. $V_H$ and $V_L$ each comprises about 110 amino acid residues, wherein three complementarity determining regions (CDR1, CDR2, and CDR3) directly involved in binding specificity with an antigen and four framework regions (FR1, FR2, FR3, and FR4) functioning as framework structures for variable regions are present. A complementary determining region is known to form conformation complementary to an antigen molecule and determine the specificity of the relevant antibody (E. A. Kabat et al., 1991, Sequences of proteins of immunological interest, Vol. 1, eds. 5, NIH publication). Whereas amino acid sequences of constant regions remain almost unchanged among antibodies of the same species, amino acid sequences of complementary determining regions are highly variable among antibodies. Hence, complementary strand determining regions are also referred to as hypervariable regions. In a variable region, such complementarity determining regions (CDRs) and framework regions are arranged in the direction from an amino acid terminus to a carboxy terminus in order of FR1, CDR1, FR2, CDR2, FR3, CDR3, and FR4. $V_L$ and $V_H$ form a dimer with each other so as to form an antigen binding site within an immunoglobulin molecule. Regarding immunoglobulin, IgG, IgM, IgA, IgE, and IgD classes are known. The antibody of the present invention may be of any class and is preferably IgG.

An antibody useful in the present invention may be derived from every animal source including birds and mammals. Examples of such the animal or bird source include mice, rats, guinea pigs, rabbits, goats, donkeys, sheep, camels, horses, chickens, and humans. Also, "monoclonal antibody" in the present invention may be chemically synthesized or synthesized using a recombinant DNA method. For example, recombinant antibodies such as chimeric antibodies and humanized antibodies are also encompassed in the present invention.

The term "chimeric antibody" refers to an antibody prepared by substituting a constant region of an antibody with a constant region of another antibody. An example of such an antibody is an antibody prepared by substituting a constant region of an anti-human CXCL1 mouse monoclonal antibody with a constant region of a human antibody. A more specific example of such an antibody is an antibody in which $V_L$ comprises any one of the amino acid sequence shown in SEQ ID NO: 10, 18, 26, 34, or 42 of $V_L$ in an anti-human CXCL1 mouse monoclonal antibody, $C_L$ comprises the amino acid sequence of $C_L$ in an arbitrary human antibody, and/or $V_H$ comprises the amino acid sequence shown in SEQ ID NO: 11, 19, 27, 35, or 43 of $V_H$ in an anti-human CXCL1 mouse monoclonal antibody, and $C_H$ comprises the amino acid sequence of $C_H$ in an arbitrary human antibody.

The term "humanized antibody" refers to a mosaic antibody prepared by artificially combining an antibody (generally a non-human antibody such as a mouse antibody)-derived CDR group with FR and a constant region of a human antibody. An example of such an antibody is an antibody prepared by combining each CDR of an anti-human CXCL1 mouse monoclonal antibody with each FR and a constant region of an arbitrary human antibody. CDR groups in a variable region are mainly responsible for the antigen-binding specificity of an antibody. Hence, when a recombinant antibody having binding properties similar to those of an antibody as described above is prepared, obtainment of the entire amino acid sequence of the antibody is not required. Specifically, by using an existing recombinant DNA technique, a mosaic antibody is prepared by substituting a DNA sequence encoding each CDR derived from an antibody with a DNA sequence encoding the corresponding CDR derived from a human antibody and then expressed. Thus, a recombinant antibody that mimics the characteristics of the antibody can be obtained. Such a technique is referred to as a CDR-grafted antibody (Nature, 1986, Vol. 321, 522). In addition, when the anti-human CXCL1 antibody or a fragment thereof of the present invention is used for detecting human CXCL1 or a fragment thereof, the antibody is not always required to be a humanized antibody. By using this grafting antibody technique, FR and a constant region may be derived from an antibody of an arbitrary non-human animal.

Furthermore, an "antibody" in the present invention may also be a multiple specific antibody. The term "multiple specific antibody" refers to a multivalent antibody that is specifically an antibody having a plurality of antigen binding sites within one molecule in which these antigen binding sites bind to different epitopes. An example of such a multivalent antibody is a bispecific antibody having two antigen binding sites such as IgG, wherein the two antigen binding sites bind to different epitopes. In the present invention, such a multiple specific antibody is preferable, in which antigen binding sites are capable of binding to different epitopes existing on human CXCL1. These antibodies can be obtained by artificially altering IgG or the like by a known method using a recombinant DNA technique.

The term "fragment thereof" in "monoclonal antibody or a fragment thereof" as used herein refers to a partial region of the antibody and specifically refers to a polypeptide chain or a complex thereof having activity substantially equivalent to the antigen-specific binding activity of the antibody. Examples of such a fragment include an antibody portion containing at least one of the above antigen binding sites and specifically, a polypeptide chain or a complex thereof having at least one $V_L$ and at least one $V_H$. Specific examples of such a polypeptide chain or a complex thereof include many sufficiently characterized antibody fragments and the like generated via cleavage of immunoglobulin with various peptidases. More specific examples of such antibody fragments include Fab, F(ab')$_2$, and Fab'. Fab is a fragment generated by cleaving an IgG molecule with papain, by which cleavage is carried out at a position closer to the N-terminal side than the disulfide linkage of a hinge part. Fab is composed of a polypeptide comprising $V_H$ and $C_H1$ which is adjacent to $V_H$ among the 3 domains ($C_H1$, $C_H2$, and $C_H3$) composing $C_H$ and a light chain. F(ab')$_2$ is a dimer of Fab', which is generated by cleaving an IgG molecule with pepsin at a position closer to the C-terminal side than the disulfide linkage of the hinge part. Fab' has a structure substantially equivalent to that of Fab, although the H chain is somewhat longer than that of Fab since it contains the hinge part (Fundamental Immunology, Paul ed., 3d ed., 1993). Fab' can be obtained by reducing F(ab')$_2$ under mild conditions and then cleaving the disulfide linkage in the hinge region. All of these antibody fragments contain antigen binding sites, so that they are capable of specifically binding to antigens (that is, human CXCL1 or a fragment thereof in the present invention).

The above "fragment thereof" in the present invention may be chemically synthesized or synthesized using a recombinant DNA method. An example of such a fragment is an antibody fragment newly synthesized using a recombinant DNA method. Specific examples of such a fragment include, but are not limited to, a monomeric polypeptide molecule prepared by artificially linking one or more $V_L$ and one or more $V_H$ of the antibody of the present invention via a linker peptide or the like having an appropriate length and sequence and a multimeric polypeptide thereof. Examples of such a polypeptide include single chain Fv (scFv: single chain fragment of variable region) (see Pierce catalog and Handbook, 1994-1995, Pierce Chemical co., Rockford, Ill.) and synthetic antibodies such as a diabody, a triabody, and a tetrabody. In an immunoglobulin molecule, $V_L$ and $V_H$ are generally separately located on different polypeptide chains (a light chain and a heavy chain). Single chain Fv is a synthetic antibody fragment that has a structure in which these variable regions are linked with a flexible linker having a sufficient length and the linked regions are contained in a single polypeptide chain. Within single chain Fv, both variable regions can be self-assembled to form a single functional antigen binding site. Single chain Fv can be obtained by incorporating a recombinant DNA encoding the single chain Fv into a phage genome using a known technique and then causing the expression of the DNA. A diabody is a molecule having a structure based on the dimeric structure of single chain Fv (Holliger et al., 1993, Proc. Natl. Acad. Sci. U.S.A., 90: 6444-6448). For example, when the length of the above linker is shorter than about 12 amino acid residues, two variable sites within single chain Fv cannot undergo self assembly. However, the two variable sites are caused to form a diabody and specifically two single chain Fvs are caused to interact with each other, enabling the assembling of $V_L$ of one Fv chain and $V_H$ of the other Fv chain. Hence, two functional antigen binding sites can be formed (Marvin et al., 2005, Acta Pharmacol. Sin., 26: 649-658). Moreover, a cysteine residue is added to the C-terminus of single chain Fv, so that disulfide bond of the two Fv chains can be formed and thereby formation of a stable diabody become possible (Olafsen et al, 2004, Prot. Engr. Des. Sel., 17: 21-27). As described above, a diabody is a divalent antibody fragment. However, each antigen binding site is not required to bind to the same epitope and may have bispecificity such that the antigen binding sites recognize and specifically bind to different epitopes. For example, one antigen binding site may comprise $V_L$ that contains CDRs comprising the amino acid sequences shown in SEQ ID NOS: 36, 37 and 38 (corresponding to CDR1, CDR2 and CDR3, respectively), and $V_H$ that contains CDRs comprising the amino acid sequences shown in SEQ ID NOS: 39, 40 and 41 (corresponding to CDR1, CDR2 and CDR3, respectively). The other antigen binding site may comprise $V_L$ that contains CDRs comprising the amino acid sequences shown in SEQ ID NOS: 28, 29 and 30 (corresponding to CDR1, CDR2 and CDR3, respectively) and $V_H$ that contains CDRs comprising the amino acid sequences shown in SEQ ID NOS: 31, 32 and 33 (corresponding to CDR1, CDR2 and CDR3 respectively). A triabody and a tetrabody have a trimeric structure and a tetrameric structure, respectively, based on a single chain Fv structure in a manner similar to a diabody. A triabody and a tetrabody are a trivalent antibody fragment and a quadrivalent antibody fragment, respectively, or may be multiple specific antibodies.

Furthermore, examples of the above "fragment thereof" include antibody fragments that are identified using phage display libraries (e.g., see McCafferty et al., 1990, Nature, Vol. 348, 522-554) and have antigen-binding capacity. In addition, also see Kuby, J., Immunology, 3$^{rd}$ ed., 1998, W. H. Freeman & Co., New York, for example.

The present invention provides an antibody or a fragment thereof having amino acid sequences composing variable regions having desirable activity to bind to human CXCL1 and CDRs thereof. Specifically, the present invention provides an antibody or a fragment thereof containing an immunoglobulin variable region comprising the amino acid sequence shown in any one of SEQ ID NOS: 4-43.

In the antibody or a fragment thereof of the present invention, CDR1, CDR2 and CDR3 can comprise the amino acid sequences shown in SEQ ID NOS: 4, 5 and 6, respectively, in its light chains, and CDR1, CDR2 and CDR3 can comprise the amino acid sequences shown in SEQ ID NOS: 7, 8 and 9, respectively, in its heavy chains.

Also, in the antibody or a fragment thereof of the present invention, $V_L$ and $V_H$ can comprise the amino acid sequences shown in SEQ ID NOS: 10 and 11, respectively.

In the antibody or a fragment thereof of the present invention, CDR1, CDR2, and CDR3 can comprise the amino acid sequences shown in SEQ ID NOS: 12, 13, and 14, respectively, in its light chains and CDR1, CDR2, and CDR3 can comprise the amino acid sequences shown in SEQ ID NOS: 15, 16, and 17, respectively, in its heavy chains.

Also, in the antibody or a fragment thereof of the present invention, $V_L$ and $V_H$ can comprise the amino acid sequences shown in SEQ ID NOS: 18 and 19, respectively.

In the antibody or a fragment thereof of the present invention, CDR1, CDR2 and CDR3 can comprise the amino acid sequences shown in SEQ ID NOS: 20, 21 and 22, respectively, in its light chains, and CDR1, CDR2 and CDR3 can comprise the amino acid sequences shown in SEQ ID NOS: 23, 24 and 25, respectively, in its heavy chains.

Also, in the antibody or a fragment thereof of the present invention, $V_L$ and $V_H$ can comprise the amino acid sequences shown in SEQ ID NOS: 26 and 27, respectively.

In the antibody or a fragment thereof of the present invention, CDR1, CDR2 and CDR3 can comprise the amino acid sequences shown in SEQ ID NOS: 28, 29 and 30, respectively, in its light chains, and CDR1, CDR2 and CDR3 can comprise the amino acid sequences shown in SEQ ID NOS: 31, 32 and 33, respectively, in its heavy chains.

Also, in the antibody or a fragment thereof of the present invention, $V_L$ and $V_H$ can comprise the amino acid sequences shown in SEQ ID NOS: 34 and 35, respectively.

In the antibody or a fragment thereof of the present invention, CDR1, CDR2 and CDR3 can comprise the amino acid sequences shown in SEQ ID NOS: 36, 37 and 38, respectively, in its light chains, and CDR1, CDR2 and CDR3 can comprise the amino acid sequences shown in SEQ ID NOS: 39, 40 and 41, respectively, in its heavy chains.

Also, in the antibody or a fragment thereof of the present invention, $V_L$ and $V_H$ can comprise the amino acid sequences shown in SEQ ID NOS: 42 and 43, respectively.

The antibody or a fragment thereof of the present invention can be modified. The term "modified or modification" used herein refers to both functional modification required for the antibody or a fragment thereof of the present invention to have activity of specifically binding to human CXCL1 (e.g., glycosylation) and modification for labeling required for detection of the antibody or a fragment thereof of the present invention. Examples of the above antibody labels include fluorescent dyes (FITC, rhodamine, Texas red, Cy3, and Cy5), fluorescent proteins (e.g., PE, APC, and GFP), enzymes (e.g., horseradish peroxidase, alkaline phosphatase, and glucose oxidase), and biotin or (strept)avidin. Also, glycosylation of the antibody of the present invention may be altered for adjusting the affinity of an antibody for a target antigen. Such alteration can be achieved by, for example, changing one or more glycosylation sites within the antibody sequence. More specifically, for example, one or more amino acid substitutions are introduced into an amino acid sequence composing one or more glycosylation sites within FR so as to remove the glycosylation sites, so that deglycosylation can be achieved at the sites. Such deglycosylation is effective for increasing the affinity of an antibody for an antigen (U.S. Pat. No. 5,714,350 and U.S. Pat. No. 6,350,861).

Monoclonal antibodies or fragments thereof to be used in the measurement method of the present invention is preferably verified before use concerning their cross-reactivity with other antigens (proteins or fragments thereof), so as to ensure their activity of specifically binding to human CXCL1 or a fragment thereof. Regarding the antibody or a fragment thereof of the present invention, examples of antigens for which cross-reactivity should be confirmed include proteins belonging to the CXC family, and particularly, a human CXCL2 protein and a human CXCL3 protein structurally analogous to human CXCL1. Also, in addition to the above proteins, other proteins having common partial structures with human CXCL1 are more preferably confirmed in advance for their cross-reactivity with antibodies or fragments thereof to be used in the measurement method of the present invention. For confirmation of cross-reactivity, an ELISA method using human CXCL1 as an antigen can be employed. At a site of reaction of an antibody to be tested for its reaction specificity, that is, an anti-human CXCL1 monoclonal antibody and a fragment thereof, with human CXCL1, another antigen protein to be confirmed for its cross-reactivity is also caused to co-exist at the reaction site. By observing the competition of them, cross-reactivity can be confirmed. Such a method for confirming cross-reactivity using the principle of competitive inhibition does not require preparation of reaction systems for all antigens, so that screening can be rapidly performed.

2. Method for Preparing Monoclonal Antibody and Hybridoma

The anti-human CXCL1 monoclonal antibody of the present invention or a hybridoma producing the antibody can be prepared by the following method, but is not limited thereto. The antibody and the hybridoma can also be prepared by any other methods known in the art.

A. Method for Preparing Anti-Human CXCL1 Monoclonal Antibody

An anti-human CXCL1 monoclonal antibody specifically binding to the partial amino acid sequence region shown in any one of SEQ ID NOS: 1-3 in the amino acid sequence composing human CXCL1 is prepared by:

a method comprising preparing a monoclonal antibody using the full-length human CXCL1 as an immunogen and then screening for an antibody specifically binding to the partial amino acid sequence region of any one of SEQ ID NOS: 1-3; or a method comprising preparing in advance a monoclonal antibody using the partial sequence of human CXCL1, which is shown in SEQ ID NO: 1, 2, or 3, as an immunogen.

A1. Preparation of Human CXCL1

First, human CXCL1 to be used as an immunogen (antigen) is prepared. Human CXCL1 may be any human CXCL1 such as natural human CXCL1, recombinant human CXCL1, or human CXCL1 prepared via chemical synthesis of a full-length or a partial amino acid sequence such as peptide synthesis.

Natural human CXCL1 can be collected from human samples including a human body fluid such as blood or urine or from supernatants of cultured human cells by the known protein separation purification techniques such as gel chromatography, ion exchange chromatography, and affinity chromatography.

Recombinant human CXCL1 can be collected by the known protein separation and/or purification techniques from cells after introduction of DNA encoding the protein into microorganisms, insect cells, or animal cells followed by expression of the DNA.

Synthetic human CXCL1 can be synthesized by techniques known in the technical field such as a solid phase peptide synthesis method, for example, using public human CXCL amino acid sequence information. Incidentally, the cDNA sequence of human CXCL1 is disclosed at GenBank under Accession No. X12510. A carrier protein such as KLH (keyhole limpet hemocyanin), OVA (ovalbumin), or BSA (bovine serum albumin) may be ligated to the synthetic human CXCL1 and then the resultant may be used.

Furthermore, when the partial sequence of human CXCL1 shown in any one of SEQ ID NOS: 1-3 is used as an immunogen, the immunogen may be a natural, recombinant, or chemically synthesized immunogen similarly to a case of immunizing with a full-length sequence.

For example, when a partial sequence of natural human CXCL1 is used as an immunogen, first, purified human CXCL1 is treated with appropriate protease such as trypsin and then peaks are isolated and fractionated using a reverse phase column. The amino acid sequence of a peptide contained in each fractionated peak is determined using a mass spectrometer. The partial sequence shown in SEQ ID NO: 1, 2, or 3 or a peak that is a portion of the partial sequence can be used as an immunogen.

Also, when a partial amino acid sequence of recombinant human CXCL1 is used as an immunogen, partial amino acid sequences shown in SEQ ID NOS: 1-3 in the above DNA sequence encoding human CXCL1 or a DNA sequence portion encoding a portion of the partial amino acid sequences is inserted into an expression vector in a manner similar to a case of preparing full-length human CXCL1 and then the vector is introduced into various cells. Hence, recombinant human CXCL1 comprising partial amino acid sequences shown in SEQ ID NOS: 1-3 or a portion thereof can be obtained.

Preparation of the partial amino acid sequences of recombinant human CXCL1, which are shown in SEQ ID NOS: 1-3 (hereinafter, referred to as partial human CXCL1 sequence (s)), is as described in detail herein.

(a) Preparation of Polynucleotide Encoding Recombinant Partial Human CXCL1 Sequence A method for preparing the polynucleotide is described in detail in Example 1 below, so that it is not mentioned herein.

As a vector to be used for expression of a partial human CXCL1 sequence, a phage or a plasmid that is capable of autonomously replicating in host microorganisms can be used. For example, examples of a plasmid include Escherichia coli-derived plasmids (e.g., pET16b, pGEX6p, pUC118, pUC119, pUC18, and pUC19), Bacillus subtilis-derived plasmids (e.g., pUB110 and pTP5), and yeast-derived plasmids (e.g., YEp13, YEp24, and YCp50). Examples of a phage include λ phages (e.g., λ gt11 and λ ZAP). Furthermore, animal viruses such as vaccinia virus and insect viruses such as baculovirus can also be used as vectors.

An example of a method for inserting a polynucleotide encoding a partial human CXCL1 sequence into the above vector comprises cleaving the purified polynucleotide with an appropriate restriction enzyme and then ligating the resultant into a vector cleaved with an appropriate restriction enzyme using DNA ligase or the like.

(b) Introduction of Partial Human CXCL1 Sequence Expression Vector Into Host

The obtained partial human CXCL1 sequence expression vector is introduced into a host that can express the human CXCL1 protein and thus a partial human CXCL1 sequence-expressing transformant is obtained. Examples of a host to be used herein are not particularly limited, as long as it is appropriate for a vector used and can express human CXCL1. For example, bacteria (e.g., Escherichia coli and Bacillus subtilis), yeast, insect cells, animal cells (COS cells and CHO cells (Journal of immunology, 1998, Vol. 160, 3393-3402)), and the like are appropriately used. Examples of a method for introducing the above vector into bacteria are not particularly limited, as long as it is a known method for introducing the vector into bacteria. Examples of such a method include a heat shock method, a method using calcium ions, and an electroporation method. All of these techniques are known in the art and are described in various documents. For example, see Sambrook, J. et al., 1989, Molecular Cloning: A Laboratory Manual Second Ed., Cold Spring Harbor Laboratory Press, Cold Spring Harbor, N.Y. Also, for transformation of animal cells, a lipofectin method (PNAS, 1989, Vol. 86, 6077), (PNAS, 1987, Vol. 84, 7413), an electroporation method, a calcium phosphate method (Virology, 1973, Vol. 52, 456-467), a DEAE-Dextran method, or the like is preferably employed.

When bacteria are used as hosts, a partial human CXCL1 sequence expression vector is preferably autonomously replicable within the bacteria and is preferably composed of a promoter sequence, a ribosome binding sequence, the DNA sequence encoding the partial human CXCL1 sequence, and a transcription termination sequence. Also, a gene encoding a regulator that controls the promoter may also be contained in the expression vector. Any promoter may be used herein, as long as it can function within a host such as Escherichia coli.

When an eukaryotic cell such as yeast, an animal cell, or an insect cell is used as a host, a partial human CXCL1 sequence-expressing transformant can be similarly obtained according to techniques known in the art. In addition to a promoter sequence and a partial human CXCL1 sequence-encoding DNA sequence, a cis element such as an enhancer, a splicing signal (e.g., a donor site, an acceptor site, and a branch point site), a polyA addition signal, a selection marker sequence, a ribosome binding sequence (SD sequence), and the like may also be ligated to a partial human CXCL1 sequence expression vector to be used in such an eukaryotic cell, if necessary.

(c) Culture of Transformant and Expression of Recombinant Partial Human CXCL1 Sequence Subsequently, the above prepared transformant is cultured. The transformant is cultured in medium according to a method that is generally employed for culturing a host. For example, when a microorganism is used as a host, examples of medium to be used herein are not particularly limited, as long as it contains carbon sources, nitrogen sources, inorganic salts, and the like, assimilable by microorganisms and enables growth and replication. Either natural or synthetic medium can be used. A more specific example of such medium is, but is not limited to, LB medium. Also, for selective culture of a transformant, antibiotics such as ampicillin or tetracycline may be added to medium, if necessary. Culture is generally carried out under aerobic conditions such as aeration and agitation culture at approximately 37° C. for 6 to 24 hours. During a culture period, pH is preferably maintained at around neutral pH. pH is adjusted using inorganic or organic acid, an alkaline solution, or the like. When a transformant is an animal cell such as a CHO cell, the host cells are seeded in DMEM (Gibco) at $1\times10^5$ cells/mL and then cultured using a 5% $CO_2$ incubator at 37° C. During culture, antibiotics such as ampicillin or tetracycline may be added to medium, if necessary.

When the above partial human CXCL1 sequence expression vector is a protein expression-inducing vector containing a protein expression control system (e.g., a repressor gene and an operator when a host is a microorganism), the above transformant should be subjected to predetermined treatment so as to induce the expression of the partial human CXCL1 sequence. A method for expression induction differs depending on a protein expression control system contained in a vector. Hence, induction treatment appropriate for each system may be carried out. For example, a protein expression control system that is the most generally used for a protein expression-inducing vector using a bacterium as a host is a system comprising a lac repressor gene and a lac operator. This system can induce expression by IPTG (isopropyl-1-thio-β-D-Galactoside) treatment. In a transformant that has a human CXCL1 expression vector containing this system, an appropriate amount (e.g., final concentration of 1 mM) of IPTG is added into medium for expression of target human CXCL1.

(d) Extraction and/or Recovery of Recombinant Human CXCL1 Partial Fragment

After culture, when the human CXCL1 partial fragment is produced within microorganisms or cells, microorganisms or cells are collected and then disrupted, so that the protein can be extracted. Also, when the human CXCL1 partial fragment is produced outside the microorganisms or cells, the culture solution is used intact or microorganisms or cells are removed by centrifugation or the like from the culture solution and then the supernatant may be used. Subsequently, general protein purification methods such as ammonium sulfate precipitation, gel chromatography, ion exchange chromatography, and affinity chromatography, are used independently or appropriately used in combination, so that human CXCL1 can be isolated and purified from the culture product. Whether or not a human CXCL1 partial fragment is obtained may be confirmed by SDS-polyacrylamide gel electrophoresis or the like.

A2. Preparation of Cells Producing Anti-Human CXCL1 Partial Sequence Antibody

The immunogen obtained in A1 is dissolved in a buffer so as to prepare an immunogen solution. At this time, an adjuvant may be added if necessary for effective immunization. Examples of such an adjuvant include commercial Freund's complete adjuvant (FCA) and Freund's incomplete adjuvant (FIA). They may be used independently or mixed and then used.

Next, the above prepared immunogen solution is administered to mammals, such as rats, mice (e.g., inbred BALB/c mice), or rabbits for immunization. Examples of a method for administration of an immunogen include, but are not limited to, subcutaneous injection using FIA or FCA, intraperitoneal injection using FIA, and intravenous injection using 0.15 mol/L sodium chloride. A single dosage of the immunogen is appropriately determined depending on animal type to be immunized, route of administration, and the like, ranging from about 30 μg to 200 μg per animal. Also, immunization intervals are not particularly limited. Immunization is carried out after primary immunization at intervals ranging from several days to several weeks, preferably ranging from 1 to 4 weeks, followed by 2 to boosters and preferably 3 to 4 boosters. After primary immunization, serum antibody titer of an immunized animal is measured by an ELISA (Enzyme-Linked Immuno Sorbent Assay) method or the like. If the antibody titer reaches a plateau, the immunogen is intravenously or intraperitoneally injected for final immunization. At 2 to 5 days after the final immunization, preferably at 3 days after the final immunization, antibody-producing cells are collected.

B. Method for Preparing Hybridoma Producing Anti-Human CXCL1 Partial-Sequence Monoclonal Antibody B1. Collection of Antibody-Producing Cell from Immunized Animal and Cell Fusion Antibody-producing cells obtained from an immunized animal are fused to myeloma cells, so that hybridomas producing a monoclonal antibody specifically recognizing the anti-human CXCL1 partial-sequence can be prepared. Examples of antibody-producing cells include spleen cells, lymph node cells, and peripheral blood cells. Spleen cells or local lymph node cells are preferable. As myeloma cells to be fused to antibody-producing cells, generally available established cell lines derived from mice or the like can be used. Cell lines to be preferably used herein have drug selectivity, are unable to survive in a HAT selective medium (containing hypoxanthine, aminopterin, and thymidine) when unfused, and are capable of growing only when fused to antibody-producing cells. Also, established cell lines to be preferably used herein are derived from animals of the same species or lines of immunized animals. Specific examples of myeloma cells include, BALB/c mouse-derived hypoxanthine, guanine, phosphoribosyltransferase (HGPRT)-deficient cell lines such as P3x62-Ag.8 (ATCCTIB9), P3x63-Ag.8. U1 (JCRB9085), P3/NSI/1-Ag4-1 (JCRB0009), P3x63Ag8. 653 (JCRB0028), and Sp2/0-Ag14 (JCRB0029).

For cell fusion of myeloma cells to antibody-producing cells, in medium for culturing animal cells, such as serum-free DMEM, or RPMI1640 medium, antibody-producing cells and myeloma cells are mixed at a ratio ranging from about 1:1 to 20:1, followed by a fusion reaction in the presence of a cell fusion accelerator. As a cell fusion accelerator, polyethylene glycol or the like with an average molecular weight ranging from 1,500 to 4,000 Da at a concentration of about 10%-80% can be used. Also, if necessary, an adjunct such as dimethyl sulfoxide may also be used in combination for enhancing fusion efficiency. Moreover, antibody-producing cells can be fused to myeloma cells using a commercial cell fusion apparatus using electrical stimulation (e.g., electroporation) (Nature, 1977, Vol. 266, 550-552).

B2. Selection of Target Hybridoma

As a method for selecting hybridomas producing a target anti-human CXCL1 partial-sequence monoclonal antibody from cells after cell fusion treatment, for example, the cell suspension is appropriately diluted with fetal calf serum-containing RPMI1640 medium or the like, cells are seeded on a 96-well microtiter plate at about $2\times10^6$ cells/well, selective medium is added to each well, and then cells are cultured while appropriately exchanging selective media. The temperature for culture ranges from 20° C. to 40° C. and is preferably about 37° C. When myeloma cells are an HGPRT-deficient cell line or thymidine kinase (TK)-deficient cell line, only hybridomas of antibody-producing cells and myeloma cells can be selectively grown and proliferated by the use of hypoxanthine, aminopterin, and thymidine-containing selective medium (HAT medium). Hence, cells that grow at around about 10 days after the start of culture in such selective medium can be selected as hybridomas.

Hybridomas selected by the use of HAT medium are first screened for using their activity of binding to natural or recombinant human CXCL1, or the amino acid sequences shown in SEQ ID NOS: 1-3 as an index. Next, hybridomas producing an antibody that has activity of binding to human CXCL1 are tested for cross-reactivity. Specifically, their activity of binding to other members of the CXC family is verified and antibodies with acceptable activity are selected. The term "acceptable cross-reactivity" refers to the ignorable degree of cross-reactivity for use as an antibody. For example, with regard to a monoclonal antibody to be used for immunoassay, it can be said that an antibody will virtually never cross-react if the signal intensity due to cross-reaction is within less than 1% of the signal intensity due to the specific reaction in the background level measured by the final measurement system.

For confirmation of reactivity to human CXCL1 or cross-reactivity to other members of the CXC family, for example, an ELISA method can be employed. In the ELISA method, a microplate is prepared by immobilizing human CXCL1 or a fragment thereof as an antigen onto the microplate and then a sample prepared by appropriately diluting a culture supernatant of the hybridoma is added to the microplate for reaction. After sufficient reaction, wells are washed and then a labeled secondary antibody against immunoglobulin is further added for reaction. The wells are washed again and then finally measurement is carried out using the label of the secondary antibody bound to the wells. Thus, the antigen binding activity of the antibody existing in the culture supernatant can be quantitatively known.

B3. Antibody Production Using Hybridoma

A hybridoma in the present invention can be used for antibody production through preparation of ascites using mice. Specifically, a hybridoma is inoculated intraperitoneally into mice whose cell used as a fusion partner upon preparation of the hybridoma or nude mice, and then ascites are appropriately collected, so that the ascites containing the antibody can be collected. More specifically, a hybridoma prepared using a Sp/0 cell as a fusion partner is inoculated intraperitoneally to BALB/c mice on day 10 after inoculation with pristane, so that ascites containing the antibody can be collected.

Also, a hybridoma in the present invention is cultured using an appropriate medium, so that it can be used for antibody production. Specifically, a hybridoma is inoculated in a hybridoma SFM medium (Gibco) at $1 \times 10^5$ cells/mL and then cultured in a 5% $CO_2$ incubator at 37° C. until the hybridomas die, so that a culture supernatant containing the antibody can be obtained, but the method is not limited thereto.

3. Method for Preparing Recombinant Anti-Human CXCL1 Partial-Sequence Monoclonal Antibody The antibody or a fragment thereof of the present invention can also be obtained by a recombinant DNA technique using a cDNA sequence encoding the amino acid sequence of a monoclonal antibody that specifically recognizes the partial human CXCL1 sequence disclosed in the present invention.

For example, by using a DNA sequence encoding the amino acid sequence that encodes a variable region of the anti-human CXCL1 partial-sequence monoclonal antibody-producing hybridoma (obtained by the technique of the aforementioned B2)-derived antibody, the nucleotide sequence of $V_H$ and the nucleotide sequence of $V_L$ are ligated to the nucleotide sequences encoding arbitrary $C_L$ and $C_H$, respectively. Thus, each polynucleotide is incorporated into an appropriate expression vector and then the vector is introduced into host cells, and thereby enabling expression of a complete immunoglobulin molecule. Also, by using a CDR grafting antibody technique, a polynucleotide encoding the amino acid sequence of CDR within a variable region obtained by the technique of the aforementioned B2 is ligated to a polynucleotide encoding each FR of an arbitrary immunoglobulin, the resultant is incorporated into an appropriate expression vector, and then the vector is introduced into host cells to obtain a complete immunoglobulin molecule by expression. Each polynucleotide can be chemically synthesized or synthesized by employing Fujimoto et al.,'s technique known as a method for synthesizing long-chain DNA (Hideya Fujimoto, Method for Preparation of Synthetic Gene, Plant Cell Engineering Series 7, Plant PCR Experimental Protocols, 1997, Shujunsha, p 95-100). Also, CDR disclosed in the present invention is derived from mouse immunoglobulin. Hence, sequences of $C_L$, $C_H$, and FR regions to be ligated are preferably derived from mice, or may be derived from other arbitrary animals such as humans. At this time, it is convenient to express a heavy chain and a light chain within the same host cell so as to enable production of a dimer comprising a heavy chain and a light chain. Specifically, for example, cells are co-transformed with a light chain expression vector and a heavy chain expression vector, and then the antibody according to the present invention can be obtained from the transformed cells. Alternatively, a polynucleotide encoding the above amino acid sequence is directly incorporated into an appropriate expression vector, and then the vector is introduced into host cells, so that the gene can be expressed as a fragment of the immunoglobulin molecule. Alternatively, as described above, polynucleotides encoding $V_L$ and $V_H$ comprising the above amino acid sequences or a light chain and a heavy chain are linked using an appropriate linker and then incorporated into a phage, so that the gene may be expressed as single chain Fv or a synthetic antibody fragment such as a diabody. Moreover, according to a phage display antibody technique (Brinkmann et al., 1995, J Immunol Methods, 182, 41-50, International Patent Publication WO97/13844, and International Patent Publication WO90-02809) developed in recent years, by which a recombinant antibody is expressed on the phage surface using genetic engineering techniques, genes encoding a heavy chain and a light chain are artificially shuffled, the varied single chain Fv antibodies are expressed as phage fusion proteins, and thus specific antibodies can also be obtained.

Preparation of a polynucleotide encoding a recombinant anti-human CXCL1 partial-sequence monoclonal antibody or a fragment thereof, preparation of a vector into which the polynucleotide is incorporated, and a method for introduction of the vector into a host may be carried out using recombinant DNA techniques known in the art as described in the aforementioned "A. Method for preparing human CXCL1 antibody." A target recombinant anti-human CXCL1 antibody or a fragment thereof can be obtained from a culture solution of transformed cells or from within the cells.

As an immunoglobulin expression vector, for example, a plasmid, a phagemid, a cosmid, a viral vector (e.g., SV40 virus-based vector, EB virus-based vector, and BPV-based vector), or the like can be used, but the examples are not limited to these vectors. For example, BCMGS Neo vector that is a kind of BPV-based vectors is a desirable vector by which a foreign gene is efficiently expressed when transformed into COST cells or the like (Hajime Karasuyama "Bovine Papilloma Virus Vector," Edited by Masami Muramatsu and Hiroto Okayama, Experimental Medicine Separate Volume: Genetic Engineering Handbook, 1991, YODOSHA (Japan), 297-299).

The above vector may also contain, in addition to a polynucleotide encoding an antibody or a fragment thereof, regulatory elements required for expression of the above antibody or the fragment thereof (e.g., a promoter, an enhancer, a terminator, a polyadenylation site, and a splicing site), or, if necessary a selection marker.

As hosts for transformation, in addition to the hosts described in the aforementioned "A. Method for preparing anti-human CXCL1 monoclonal antibody," Sp2/0 (mouse myeloma) cells (European Journal of Cancer Research Preview (1996) Vol. 5, 512-519; Cancer Research (1990) Vol. 50, 1495-1502) are appropriately used.

In the present invention, host cells containing a vector for expression of an antibody or a fragment thereof are cultured according to a conventional method, so that the antibody can be produced in the resulting culture supernatant or within the host cells. Specifically, when CHO cells are used as host cells, host cells are seeded in DMEM (Gibco) at $1 \times 10^5$ cells/mL and then cultured in a 5% $CO_2$ incubator at 37° C., so that a culture supernatant containing the antibody can be obtained. Also, for example, when a host cell is *Escherichia coli*, cells are seeded and cultured in general medium such as LB medium that is used for culturing *Escherichia coli* and then protein expression is induced, so that the antibody can be produced in the resulting culture supernatant or within the host cells.

When an antibody or a fragment thereof that is an expression product contains a constant region, the antibody or a fragment thereof can be purified and/or collected using a protein A column, a protein G column, an anti-immunoglobulin antibody affinity column, or the like from the culture supernatant or the cell lysate. Meanwhile, when such an expression product is expressed in a form composed of variable regions alone, and thus containing no constant region, the above purification method cannot be applied. Hence, other appropriate purification methods are applied. For example, an antibody or a fragment thereof is expressed as a structure, in which a tag sequence that is advantageous for purification, such as a histidine tag, is fused to the C terminus, so that the expression product can be purified by affinity chromatography using a corresponding ligand. If the expression product is not the above tag fusion protein, it can be purified according to a conventional method for protein purification, such as ammonium sulfate precipitation, ion exchange chromatography, reverse phase chromatography, gel filtration chromatography, or hydroxyapatite chromatography.

4. Confirmation of Epitope on Human CXCL1 Recognized by the Obtained Anti-Human CXCL1 Monoclonal Antibody An epitope on human CXCL1 recognized by the obtained anti-human CXCL1 monoclonal antibody can be confirmed by the following method.

First, human CXCL1 subjected to reductive alkylation is reacted with an anti-human CXCL1 monoclonal antibody so that an antigen-antibody complex is formed. Then proteolytic treatment is carried out using appropriate protease such as trypsin. The antibody is not easily digested with trypsin when proteolytic treatment is carried out. Hence, the antigen-antibody complex can be collected using Protein G sepharose or the like. At this time, an antigen, other than a portion protected by binding to the antibody, is digested by protease treatment. Accordingly, the collected antigen-antibody complex is analyzed by LC-MS, so that such a portion protected by binding to the antibody, i.e., an epitope on human CXCL1 to be recognized by the antibody can be identified.

Furthermore, an epitope on human CXCL1 to be recognized by the anti-human CXCL1 monoclonal antibody can also be confirmed, for example, by a competitive method using a synthetic peptide. First, a synthetic peptide with 4 to 8 amino acids each of the amino acid sequence composing human CXCL1 are prepared by a solid phase synthesis method, or the like. In an experiment for confirmation of the binding to human CXCL1 with the use of the above ELISA method, when the anti-human CXCL1 monoclonal antibody is reacted with immobilized human CXCL1, the synthesized peptide is caused to act. If inhibition of the binding of the anti-human CXCL1 monoclonal antibody is confirmed, it can be concluded that the amino acid sequence of the synthesized peptide is an epitope recognized by the anti-human CXCL1 monoclonal antibody.

5. Method for Detecting Human CXCL1

In the present invention, an immunoassay method for human CXCL1 can be realized by the use of the obtained monoclonal antibody or a fragment thereof. The measurement method of the present invention is excellent in specificity to human CXCL1, so that an immunoassay method ideal for human CXCL1 can be provided.

The term "sample(s)" to be used in the measurement method of the present invention refers to various samples that can contain human CXCL1. Examples of such a sample include cultured cells containing DNA encoding human CXCL1 or a fragment thereof, a cultured cell lysate, a culture supernatant, and a human sample. The term "human sample" refers to every human-derived biological samples such as tissue collected from a human (e.g., tissue collected after an operation) and body fluids such as blood, serum, blood plasma, urine, a spinal fluid, saliva, a lymph fluid, a lacrimal fluid, and a seminal fluid. Preferably, such a sample is blood, serum, blood plasma, or urine. Further, a sample in the present invention may not only be a liquid sample, but also a solid sample. For example, a tissue section sample can be used. The method for measuring human CXCL1 of the present invention is conveniently carried out for a tissue section sample, since the presence or the absence of and localization of human CXCL1 can be observed in situ by the method.

The present invention is characterized by using a combination of two or more types and preferably 2 types of the above anti-human CXCL1 partial-sequence monoclonal antibody or a fragment thereof, which specifically recognize any one sequence region of the amino acid sequences shown in SEQ ID NOS: 1-3 that are partial sequences of the amino acid sequence composing human CXCL1, and specifically recognize sequence regions differing from each other. More preferably the present invention is characterized by using such a combination containing an anti-human CXCL1 monoclonal antibody that specifically recognizes the amino acid sequence region shown in SEQ ID NO: 3. Combinations of anti-human CXCL1 partial-sequence monoclonal antibodies or fragments thereof recognizing different amino acid sequence regions of human CXCL1 contribute to improvement in detection sensitivity for human CXCL1.

The immunoassay of the present invention can be carried out by a known immunoassay method using a labeled antibody, such as an ELISA method, an EIA method, a fluorescence immunoassay method, a radioimmunoassay method, or a luminescence immunoassay method, or, a surface plasmon resonance method (SPR method), a quartz crystal microbalance method (QCM method), or the like. The immunoassay method of the present invention can be preferably applied in an immunoassay method using a labeled antibody.

The ELISA method is also referred to as an enzyme-linked immunosorbent analysis method, which is a method for quantitating a target antigen comprising detecting a trace amount of a target antigen contained in a sample using an enzyme-labeled antibody or antigen and the action of the enzyme in the form of color optical density or fluorescence intensity in an antigen-antibody reaction. Specifically, the method comprises immobilizing the antibody or a fragment thereof of the present invention, or human CXCL1 or a fragment thereof on a solid-phase support and then enzymatically detecting an immunological reaction between the antibody or the like and human CXCL1 or the like. Examples of such a method include a direct method, an indirect method, and a sandwich method. The present invention is applied to the sandwich method. Regarding measurement methods for the ELISA method, see known methods (Edited by Japanese Society of Laboratory Medicine "Clinical Pathology Extra Special Edition No. 53, Immunoassay for Clinical Examination—Technology and Application-," The Clinical Pathology Press, 1983; Edited by Eiji Ishikawa et al., "Enzyme Immunoassay," Third Edition, IGAKU-SHOIN, 1987; Edited by Tsunehiro Kitagawa et al., "Protein Nucleic Acid Enzyme Separate Volume No. 31 Enzyme Immunoassay," KYORITSU SHUPPAN CO., LTD, 1987; Edited by Minoru Irie "Radioimmunoassay," Kodansha Scientific Ltd., 1974; and Edited by Minoru Irie "Radioimmunoassay Part II," Kodansha Scientific Ltd., 1979). As the above solid-phase support, insoluble supports in the shapes of beads, microplates, test tubes, sticks, test specimens or the like made of material such as polystyrene, polycarbonate, polyvinyl toluene, polypropylene, polyethylene, polyvinyl chloride, nylon, polymethacrylate, latex, gelatin, agarose, cellulose, sepharose, glass, metal, ceramics, magnetic material, or the like can be used. Immobilization of the antibody or a fragment thereof or human CXCL1 or a fragment thereof of the present invention onto a solid-phase support can be achieved by binding according to a known method such as a physical adsorption method, a chemical binding method, or a combination of these methods.

As the above labeling substance, for example: in the case of the ELISA method, peroxidase (POD), alkaline phosphatase, β-galactosidase, urease, catalase, glucose oxidase, lactate dehydrogenase, amylase, a biotin-avidin complex, or the like; in the case of a fluorescence immunoassay, fluorescein isothiocyanate, tetramethylrhodamine isothiocyanate, substituted rhodamine isothiocyanate, dichlorotriazine isothiocyanate, Alexa480, AlexaFluor488, or the like; or in the case of a radioimmunoassay, tritium, iodine 125, iodine 131, or the like can be used. However, examples of such a labeling substance are not limited to these examples.

As a luminescence immunoassay, an NADH-FMNH$_2$-luciferase system, a luminol-hydrogen peroxide-POD system, an acridinium ester system, a dioxetane compound system or the like can be used. As a method for binding a labeled antigen and an antibody, in the case of the ELISA method, a known method such as a glutaraldehyde method, a maleimide method, a pyridyl disulfide method, or a periodic acid method and in the case of a radioimmunoassay, a known method such as a chloramine T method or Bolton-Hunter method can be used.

Furthermore, the immunoassay method of the present invention can also be carried out by measuring visually or through the use of an optical method transmitted light or scattered light representing the generation of immune complex agglutinates resulting from immunonephelometry, latex agglutination reaction, latex turbidimetry, a hemagglutination reaction, a particle agglutination reaction, or the like. In such a case, as a solvent, a phosphate buffer, a glycine buffer, a tris buffer, Good's buffer, or the like can be used. Furthermore, a reaction accelerator such as polyethylene glycol or a non specific reaction inhibitor may also be contained.

In the immunoassay method of the present invention, 2 types are preferably selected from among the 3 types of the above anti-human CXCL1 partial-sequence monoclonal antibodies or fragments thereof and then used. Regarding specific methods, a case, in which a monoclonal antibody specifically recognizing the amino acid sequence region shown in SEQ ID NO: 1 and a monoclonal antibody specifically recognizing the amino acid sequence region shown in SEQ ID NO: 3 are used, is described as an example. However, the embodiment of the present invention is not limited to this example.

For example, when the immunoassay method of the present invention is applied to a sandwich method of the ELISA method, first, the monoclonal antibody specifically recognizing the amino acid sequence region shown in SEQ ID NO: 1 is immobilized onto an insoluble support. Either one type or several types of antibody may be immobilized, as long as it (they) specifically recognizes the amino acid sequence region shown in SEQ ID NO: 1. Next, a sample containing human CXCL1 is caused to act on the surface on which the antibody has been immobilized, so that a complex of the immobilized antibody and human CXCL1 is formed on the support surface. Subsequently, unbound substances other than human CXCL1 existing in the sample are removed by sufficient washing with a cleaning fluid. Furthermore, a labeled monoclonal antibody that specifically recognizes the amino acid sequence region shown in SEQ ID NO: 3 is prepared and then the labeled antibody is caused to act on a support to which a complex of the immobilized antibody and human CXCL1 has bound. After sufficient washing with a cleaning fluid, detection is carried out using the label, so that human CXCL1 existing in the sample can be detected. At this time, either one type of or several types of labeled antibody may be used herein, as long as it (they) is a monoclonal antibody specifically recognizing the amino acid sequence region shown in SEQ ID NO: 3. Two or more types of labeled antibody are preferably used and 2 types of labeled antibody are more preferably used. Also, when an animal species, from which the monoclonal antibody specifically recognizing the amino acid sequence region shown in SEQ ID NO: 1 is derived, differs from an animal species, from which the monoclonal antibody specifically recognizing the amino acid sequence region shown in SEQ ID NO: 3 is derived, detection can also be carried out using a labeled secondary antibody that recognizes the antibody specifically recognizing the amino acid sequence region shown in SEQ ID NO: 3, without labeling the monoclonal antibody specifically recognizing the amino acid sequence region shown in SEQ ID NO: 3.

The above description similarly applies to a case in which a monoclonal antibody specifically recognizing the amino acid sequence region shown in SEQ ID NO: 2 is used. Also, antibodies used for immobilization and labeling can be conversely used for labeling and immobilization, respectively.

A labeled antibody and a sample containing human CXCL1 are mixed in advance so as to form an antigen-antibody complex and then the complex can be caused to act on the immobilized antibody. If an antibody to be immobilized is biotin-labeled, the biotinylated immobilized antibody, a sample containing human CXCL1, and an antibody labeled with a label other than biotin are mixed together, so as to form an antigen-antibody complex. Subsequently, the complex is caused to act on a support on which avidin has been immobilized, so that the antigen-antibody complex can be detected using labeling other than biotinylation.

Furthermore, test strips for immunochromatography can also be used for the immunoassay method of the present invention. Such a test strip for immunochromatography comprises, for example, a sample-receiving part made of material that can easily absorb a sample, a reagent part containing the labeled diagnostic agent of the present invention, a development part in which a reaction product of a sample and the diagnostic agent migrates, and a display part for capturing the reaction product that has been developed, resulting in color development. A commercial diagnostic of pregnancy or the like has a form similar to the above. The principle of the measurement method is as described below. First, a sample is applied to the sample-receiving part, and the sample-receiving part absorbs the sample and then causes the sample to reach a reagent part. Subsequently, at the reagent part, human CXCL1 in the sample reacts with the above labeled anti-human CXCL1 partial-sequence monoclonal antibody or a fragment thereof by an antigen-antibody reaction, and then the formed reaction complex migrates in the development part to reach the display part. At the display part, the above reaction complex reacts with another type of anti-human CXCL1 partial-sequence monoclonal antibody which is different from the labeled monoclonal antibody and recognizes another CXCL1 partial-sequence and then the reaction complex is captured, so that coloration resulting from the label of the reaction complex is observed. The above test strip for immunochromatography exerts an extremely low degree of invasiveness, bringing neither pain nor risk due to the use of reagents to users. Hence, such a test strip can be used for monitoring in homes. The results of monitoring are subjected to close investigation and/or treatment (e.g., surgical excision) at the level of each medical institution, making it possible to lead the results to prevention of metastases and/or recurrence. Also currently, the test strip can be mass-produced at low cost, for example, by the production method as disclosed in JP Patent Publication (Kokai) No. 10-54830 A (1998).

A case in which the monoclonal antibody specifically recognizing the amino acid sequence region shown in SEQ ID NO: 1 and the monoclonal antibody specifically recognizing the amino acid sequence region shown in SEQ ID NO: 3 are used is as described below, as an example. First, a sample containing human CXCL1 is applied to a sample-receiving part and then the sample-receiving part absorbs the sample to cause the sample to reach a reagent part. Subsequently, at the reagent part, urothelial cancer cell-derived human CXCL1 in the sample reacts with the monoclonal antibody specifically recognizing the labeled amino acid sequence region shown in SEQ ID NO: 1 of the present invention. A complex resulting from the reaction migrates in the development part to reach a display part. At the display part, the above reaction complex reacts with the monoclonal antibody specifically recognizing the amino acid sequence region shown in SEQ ID NO: 3, so that coloration is observed.

As the measurement method of the present invention, a surface plasmon resonance method (SPR method) can be employed. The term "surface plasmon resonance phenomenon" refers to a phenomenon by which reflected light intensity was significantly attenuated by laser irradiation to a metal thin film at a specific angle of incidence (resonance angle). An SPR sensor using the principle of the SPR phenomenon is capable of measuring adsorbed material on the metal thin film surface with high sensitivity. Therefore, an antibody and/or a target antigen is immobilized in advance onto the metal thin film surface and then the sample is caused to pass over the metal thin film surface. This makes it possible to detect the difference between the amount of a substance adsorbed onto the metal surface before the passage of the sample and such amount after the passage of the sample. A substitution method, an indirect competitive method, and the like are known and any of these methods may be employed. These techniques are known in the art. For example, see Kazuhiro Nagata and Hiroshi Handa, Experimental Method for Real-time Analysis of Biomaterial Interaction, Springer-Verlag Tokyo, Tokyo, 2000.

Furthermore, for the measurement method of the present invention, a quartz crystal microbalance method (QCM method) can also be employed. This method uses a phenomenon such that when a substance adsorbs to the surface of an electrode attached to a quartz oscillator, the resonance frequency of the quartz oscillator decreases depending on the mass. A QCM sensor using the method is a mass measurement sensor capable of quantitatively capturing an extremely trace amount of an adsorbed substance based on an amount of change in water resonance frequency. This technique is known in the art. For example, see J. Christopher Love, L. A. Estroff, J. K. Kriebel, R. G. Nuzzo, G. M. Whitesides, 2005, Self-Assembled Monolayers of a Form of Nanotechnology, Chemical Review, 105: 1103-1169; Toyosaka Morizumi, Takamichi Nakamoto, 1997, Sensor Engineering, Shokodo Co., Ltd., for example.

6. Human CXCL1 Detection Kit

The present invention can be used as a kit for carrying out these immunological measurement methods. Specifically, not only the antibody or a fragment thereof of the present invention, but also a labeled secondary antibody, furthermore a substrate required for detection of a label, a positive control and a negative control, a buffer to be used for dilution or washing of samples, and the like may be combined to form a kit.

EXAMPLES

The present invention will be further described specifically by referring to examples. However, the present invention is not limited by these examples.

Example 1

Preparation of Recombinant Human CXCL1 Using *Escherichia coli*

(Preparation of Human CXCL1 Gene)

To prepare recombinant human CXCL1 to be used as an immunogen for an antibody, first, human CXCL1 mRNA was prepared from HEK293 cells. mRNA was prepared using Qiashredder and RNeasy mini kit (Qiagen) according to the included protocols regarding details.

Next, cDNA was synthesized using the obtained total mRNA as a template with reverse transcriptase SuperscriptII (Invitrogen), so that a human cDNA library was constructed. A reverse transcription reaction was carried out according to protocols included with the above enzyme.

Subsequently, PCR was carried out using the obtained human cDNA library as a template and a primer set consisting of the nucleotide sequences shown in SEQ ID NOS: 44 and 45. The nucleotide sequence shown in SEQ ID NO: 44 contains a portion of the 5' terminal region of the human CXCL1 gene and an Nde I recognition sequence on the upstream side. The nucleotide sequence shown in SEQ ID NO: 45 contains a portion of the 3' terminal region of the human CXCL1 gene and a BamH I recognition sequence on the downstream side. A PCR solution containing KOD DNA polymerase (Toyobo Co., Ltd.) as DNA polymerase, 10 ng of a cDNA library and 10 pmol of each primer was prepared according to protocols included with KOD. Regarding reaction conditions, after 10 minutes of heating at 94° C., a cycle consisting of 94° C. for 30 seconds, 55° C. for 30 seconds, and 72° C. for 1 minute was repeated 30 times, and then finally the temperature was kept at 72° C. for 4 minutes. The amplified DNA fragment was purified using Quantum prep PCR Kleen Spin Columns (Bio-rad). A PCR product with a full length of about 300 bp was obtained by the reaction.

A ligation reaction was carried out to incorporate the obtained DNA fragment into open circular pUC118 (Takara Bio Inc.) cleaved with Hinc II and treated with BAP. Ligation High (Toyobo Co., Ltd.) was used as DNA ligase. The reaction was carried out according to the included protocols. Subsequently, competent cells were transformed using the solution obtained after the ligation reaction. As the competent cells, an *Escherichia coli* strain, DH5α (Takara Bio Inc.), was used. Transformation was specifically carried out according to the included protocols. Transformed cells were applied to an LB plate containing antibiotic ampicillin at a concentration of 100 μg/mL and then cultured overnight at 37° C. The obtained transformant was cultured overnight at 37° C. in LB liquid medium containing 100 μg/mL ampicillin. Target pUC118_CXCL1 was obtained by Mini-Prep.

Next, pUC118_CXCL1 was cleaved with restriction enzymes, Nde I and BamH I and then the reaction solution was subjected to agarose electrophoresis. After electrophoresis, an about 300-bp fragment confirmed by ultraviolet irradiation was excised from the gel and then the DNA fragment was extracted. Extraction was carried out using a PCR GFX Column (GE HEALTHCARE BIO-SCIENCES). For incorporation of the extracted DNA fragment into an expression vector pET16b (Novagen) (roughly 6-kb fragment) that had been cleaved with Nde I/BamH I, a ligation reaction was carried out. Subsequently, transformation of DH5α using the solution obtained after the ligation reaction, culturing of the transformant, and Mini-Prep were carried out. Thus, target pET16b_CXCL1 was obtained. Each step was carried out according to the above methods.

(Preparation of Recombinant Human CXCL1)

For preparation of recombinant human CXCL1, an *Escherichia coli* strain, Rosetta-Gami 2 (Novagen), was transformed with pET16b_CXCL1. The obtained transformant was pre-cultured overnight at 37° C. in 30 mL of LB medium containing ampicillin and chloramphenicol. Next, the pre-cultured transformant was inoculated into 3 L of the same medium and then cultured at 37° C. for 3 hours. IPTG with a final concentration of 1 mM was added, culture was carried out at 32° C. for 6 hours, the expression of target recombinant human CXCL1 was induced, and thus microorganisms were collected by centrifugation.

The obtained microorganisms were washed with PBS and then an insoluble fraction was prepared as a precipitate using B-PER (PIERCE). Specific procedures were carried out according to the included protocols. Next, the insoluble fraction was solubilized using an inclusion body solubilization reagent (PIERCE) and then histidine tag-fused human CXCL1 was adsorbed using TALON Metal Affinity Resin (CLONETECH). The protein-adsorbed resin was washed with PBS containing 10 mM imidazole and then eluted using a 1 M imidazole solution.

Next, protein refolding was carried out using the obtained elution fraction. First, the fraction was dialyzed overnight against a PBS solution containing 6 M urea. Until the final concentration of urea in the dialysis solution reached 1 M, PBS was added stepwise to the dialysis solution for dilution. Finally, dialysis was carried out overnight against a newly prepared PBS solution. The obtained refolding solution was subjected to acrylamide gel electrophoresis. Purification of histidine tag-fused human CXCL1 with a molecular weight of about 10,000 Da was confirmed by Coomassie brilliant blue staining.

Example 2

Preparation and Selection of Mouse Monoclonal Antibody Against Human CXCL1

(Preparation of Anti-Human CXCL1 Antibody-Producing Mouse)

100 μL of 0.3 mg/mL human CXCL1 solution obtained in Example 1 was mixed with 100 μL of MPL+TDM Emulsion (Corixa). The total amount of the solution was administered intraperitoneally to a 7-week-old BALB/c mouse. After 2 weeks and after 4 weeks, the same amount of a similarly prepared human CXCL1 solution was administered. Subsequently, 100 μL of blood was collected from the mouse via the caudal vein, left to stand overnight, and then centrifuged at 5000×g for 5 minutes. Thus, a supernatant was collected as blood plasma.

100 μL of 1 μg/mL human CXCL1 solution was added to each well of a 96-well polystyrene plate (Greiner Bio-One) and then immobilized overnight. After the protein solution in each well was discarded, 200 μL of a BlockAce solution (Dainippon Sumitomo Pharma Co., Ltd.) diluted 4-fold was poured thereinto, and then the plate was left to stand for 1 hour at room temperature. Subsequently, the plate was washed with PBS-T, so that a human CXCL1-immobilized plate was prepared. The above obtained blood plasma was diluted 100-fold, 100 μL of the diluted blood plasma was added to each well of the human CXCL1-immobilized plate, and then the plate was left to stand at room temperature for 1 hour. Subsequently, the solution in each well was discarded and then the plate was washed with PBS-T. 100 μL of an HRP-labeled anti-mouse IgG solution (Dako) was added and then the plate was left to stand at room temperature for 1 hour. The solution in each well was discarded. After washing with PBS-T, 100 μL of a TMB solution was added and allowed to react for 15 minutes. Color development due to the reaction was confirmed at an absorbance of 450 nm. Based on color development, it was determined that the antibody against human CXCL1 had been produced in a blood sample.

(Preparation of Anti-Human CXCL1 Monoclonal Antibody)

A human CXCL1 solution prepared in a manner similar to the above was administered intraperitoneally to a mouse for which production of the antibody against human CXCL1 had been confirmed. After 3 days, a splenectomy was carried out. A hole was made in the resected spleen using a syringe, and then RPMI1640 medium (GIBCO) was injected through the hole so as to extrude spleen cells, and thus a spleen cell solution was obtained. The obtained spleen cell solution was centrifuged at 1200 rpm for 7 minutes. A supernatant was removed and then washed with RPMI1640 medium. The supernatant was suspended again in RPMI1640 medium, the number of cells was counted, and thus an SP2/0 myeloma cell solution containing ⅒ of the total number of spleen cells was prepared. Both cell solutions were mixed, the mixture was centrifuged at 2200 rpm for 10 minutes, and then the supernatant was discarded. Cells were loosened by tapping, 1 mL of the solution prepared by mixing PEG (ROCHE) with HBSS (GIBCO) at 5:1 was added to the cells, and then the mixture was stirred. In the following procedures, unless otherwise specified, solutions or media were always kept at 37° C. and then used.

RPMI1640 medium (9 mL) was slowly added to a cell solution supplemented with PEG and HBSS for 5 minutes. The mixture was gently mixed, and then it was centrifuged at 2200 rpm for 10 minutes. A supernatant was removed. The obtained precipitated cells were suspended in RPMI1640 medium supplemented with 15% FCS and HAT (ROCHE)

and then 200 μL of the suspension was poured per well into a 96-well cell culture plate (Greiner Bio-One), followed by 1 week of culture at 37° C. under 5% $CO_2$.

Colonies grown under conditions of supplementation with HAT were determined to be hybridomas of spleen cells fused to myeloma cells. The supernatant of each well in which such colonies had been grown was diluted 5-fold. 100 μL of the diluted solution was added to each well of the human CXCL1-immobilized plate and then the presence or the absence of antibody production was confirmed by a method similar to the above. Wells for which antibody production had been confirmed were determined to be positive. Colonies in positive wells were suspended in RPMI medium containing 15% FCS and HT (Invitrogen) and then cloning of positive clones was carried out by a limiting dilution method. 75 types of hybridoma obtained as a result of cloning were acclimatized to SFM medium (GIBCO) and then antibody production was carried out. Hybridomas were inoculated into 60 mL of 100% SFM medium at $1 \times 10^5$ cells/mL and then cultured for 10 days until cells died. Each culture solution was centrifuged at 3000 rpm for 15 minutes, so as to remove cells. The obtained culture supernatant was subjected to purification of antibodies contained therein using a MabTrap Kit (GE HEALTHCARE BIO-SCIENCES).

(Selection of Anti-Human CXCL1 Monoclonal Antibody)

For the above purified 75 types of antibody, an antibody having high affinity for human CXCL1 was selected by the following methods. First, a 10 μg/mL solution was prepared for each purified antibody. The solution was poured into a 96-well polystyrene plate (Greiner Bio-One) at 100 μL, per well, followed by overnight immobilization. After the purified antibody solution in each well was discarded, 200 μL of a BlockAce solution (Dainippon Sumitomo Pharma Co., Ltd.) diluted 4-fold was poured and then left to stand for hour at room temperature. Subsequently, the solution was discarded, the plate was washed with PBS-T, and thus a plate on which the purified antibody had been immobilized was prepared. Next, recombinant human CXCL1 was serially diluted from 1000 pg/mL to 15 pg/mL to prepare an antigen solution. The antigen solution was added to the above plate onto which the purified antibody had been immobilized at 100 μL per well, followed by 1 hour of reaction at room temperature. Subsequently, the antigen solution was discarded, the plate was washed with PBS-T, and then 100 μL of 50 μg/mL biotin-labeled anti-human CXCL1 polyclonal antibody (R&D SYSTEMS) was added to each well, followed by 1 hour of reaction at room temperature. The solution within each well was discarded, the plate was washed with PBS-T, and then 100 μA of an avidin-HRP solution (R&D SYSTEMS) was allowed to react for 30 minutes at room temperature. Moreover, the avidin-HRP solution was discarded, the plate was washed with PBS-T, and then 100 μL of a TMB solution was added, followed by 15 minutes of reaction. The reaction was stopped by addition of 100 μA of a 2N sulfuric acid solution. Color development was confirmed by measuring absorbance at 450 nm. Purified antibodies in wells for which color reaction had occurred strongly were determined to have high affinity for human CXCL1. As a result, 5 types of antibody, IgG1-1, IgG1-3, IgG1-10, IgG1-14, and IgG2b-1, were selected.

(Determination of Light Chain and Heavy Chain cDNA Sequences and Amino Acid Sequences of Monoclonal Antibody Using Hybridoma)

For the selected 5 types of antibody, light chain and heavy chain cDNA sequences and amino acid sequences were determined. First, a hybridoma producing each antibody was cultured using RPMI1640 medium supplemented with 15% FCS at 37° C. under 5% $CO_2$ until reaching a concentration of $1 \times 10^6$ cells/mL. Subsequently, the culture solution was centrifuged at 1200 rpm for 5 minutes and then cells were collected. mRNA was prepared from the collected hybridomas. Preparation was carried out using Qiashredder and a RNeazy mini kit (Qiagen) according to the included protocols regarding details. Next, cDNA was synthesized using the obtained Total mRNA as a template and Oligo dT primer with reverse transcriptase SuperscriptII (Invitrogen), so that a cDNA library was constructed.

Next, PCR was carried out using the cDNA library obtained for each hybridoma as a template and Mouse Ig Primer (Novagen). The amplification product (mouse immunoglobulin variable region cDNA) was inserted to the EcoR I site of ZERO BLUNT PCR TOPO Vector (Invitrogen) for ligation. Ligation was carried out using Ligation High (Toyobo Co., Ltd.) according to the included protocols. With a ligation reaction solution, competent cells were transformed. As competent cells, DH5α (Takara Bio Inc.) was used according to the included protocols regarding details. Transformed cells were applied to an LB plate containing 100 μg/mL ampicillin and then cultured at 37° C. overnight. Four clones of the transformant derived from each amplification product were inoculated into LB liquid medium containing 100 μg/mL ampicillin and then cultured at 37° C. overnight. As a result of preparation of a vector DNA solution from each culture solution by Mini-Prep, 4 types of vector solution in which DNA encoding a monoclonal antibody had been incorporated were obtained for each amplification product.

The obtained vector solutions were subjected to DNA sequence analysis of a region encoding a monoclonal antibody using an M13 primer. Analysis was conducted using a 3130×1 genetic analyzer (Applied Biosystems). Clones having no stop codon within the insertion region were determined to be DNA sequences encoding target monoclonal antibodies. Light chain and heavy chain DNA sequences of the above 5 antibodies (IgG1-1, IgG1-3, IgG1-10, IgG1-14, and IgG2b-1) were determined. For the determined DNA sequences, amino acid sequences to be encoded were determined depending on codon usage frequency in *Escherichia coli*, so that the sequences shown in SEQ ID NOS: 4-43 could be obtained.

The amino acid sequences shown in SEQ ID NOS: 36-43 were obtained as amino acid sequences encoding IgG1-1. More specifically, SEQ ID NOS: 36, 37, and 38 encode light chain CDR1, CDR2, and CDR3 of IgG1-1, respectively. Also, SEQ ID NOS: 39, 40, and 41 encode the heavy chain CDR1, CDR2, and CDR3 of the same IgG1-1, respectively. Also, SEQ ID NOS: 42 and 43 encode the full-length light chain variable region and the full-length heavy chain variable region of IgG1-1, respectively.

The amino acid sequences shown in SEQ ID NOS: 28-35 were obtained as the amino acid sequences encoding IgG1-3. More specifically, SEQ ID NOS: 28-33 encode light chain CDR1-3 and heavy chain CDR1-3 of IgG1-3 in this order. Also, SEQ ID NOS: 34 and 35 encode the full-length light chain variable region and the full-length heavy chain variable region of IgG1-3, respectively.

The amino acid sequences shown in SEQ ID NOS: 4-11 were obtained as the amino acid sequences encoding IgG1-10. More specifically, SEQ ID NOS: 4-9 encode light chain CDR1-3 and heavy chain CDR1-3 of IgG1-10 in this order. SEQ ID NOS: 10 and 11 encode the full-length light chain variable region and the full-length heavy chain variable region of IgG1-10, respectively.

The amino acid sequences shown in SEQ ID NOS: 20-27 were obtained as the amino acid sequences encoding IgG1-14. More specifically, SEQ ID NOS: 20-25 encode light chain CDR1-3 and heavy chain CDR1-3 of IgG1-14 in this order. SEQ ID NOS: 26 and encode the full-length light chain variable region and the full-length heavy chain variable region of IgG1-14, respectively.

The amino acid sequences shown in SEQ ID NOS: 12-19 were obtained as the amino acid sequences encoding IgG2b-1. More specifically, SEQ ID NOS: 12-17 encode light chain CDR1-3 and heavy chain CDR1-3 of IgG2b-1 in this order. SEQ ID NOS: 18 and encode the full-length light chain variable region and the full-length heavy chain variable region of IgG2b-1, respectively.

Example 3

Analysis of Partial Human CXCL1 Sequence Recognized by Selected Antibody

Regarding the 5 antibodies selected in Example 2, an epitope on the human CXCL1 amino acid sequence recognized by each antibody is analized.

First, DTT was added to 100 µL of a 1 µg/µL human CXCL1 solution to a final concentration of 10 mM. A reaction was carried out at 95° C. for 5 minutes for reduction of disulfide bonds within CXCL1. Next, iodoacetamide with a final concentration of 20 mM was added and then an alkylation reaction of thiol groups was carried out under light shielding conditions at 37° C. for 30 minutes. The 20 µg of each antibody selected in Example 2 was added to the obtained 12 µg of reduced and alkylated human CXCL. Tris-HCl buffer (100 mM, pH 8.0) was added to each mixture to a volume of 100 µL, followed by 1 hour of reaction at room temperature while stirring and mixing.

Next, trypsin (Promega), aminopeptidase M (ROCHE), and carboxypeptidase Y (ROCHE) were added to final concentrations of 0.2 µg, 0.5 µU, and 0.02 respectively, followed by 2 hours or more of reaction at 37° C. Each reaction solution was mixed with Protein A-glass beads (GE HEALTHCARE BIO-SCIENCES) that had been blocked in advance with 1% BSA-PBS and then washed with PBS in NP-40 buffer (100 mM Tris-HCl buffer (pH8.0), 5 mM EDTA, 150 mM NaCl, 1% NP-40), followed by 30 minutes of reaction at 4° C.

The reaction solutions were each washed with 25 mM ammonium carbonate buffer (pH8.0). An antigen-antibody complex was eluted using 100 µL of 0.1% formic acid. Eluates were subjected to LC-MS analysis with a Q-TOF Premier (Waters-MicroMass). LC-MS analysis was carried out according to protocols included with the instrument.

As a result, the partial human CXCL1 sequence recognized by each antibody obtained Example 2 was revealed and is shown in Table 1.

Reference Example 1

Analysis of Partial Human CXCL1 Sequence Recognized by Commercial Antibody

A monoclonal antibody included as an antibody for immobilization in a commercial human CXCL1 detection kit, Human CXCL1/GRO alpha DuoSet (R&DSYSTEMS), was subjected to analysis of an epitope on the human CXCL1 amino acid sequence recognized in a manner similar to Example 3.

As a result, the partial human CXCL1 sequence recognized by the commercial antibody was revealed and is shown in Table 1.

TABLE 1

| Antibody name | Sequence | SEQ ID NO: |
|---|---|---|
| IgG1-1 (Example 3) | NGRKACLNPASPIVKKIIEKMLNSDKSN | 3 |
| IgG1-3 (Example 3) | SPGPHCAQTEVIATLK | 2 |
| IgG1-10 (Example 3) | NGRKACLNPASPIVKKIIEKMLNSDKSN | 3 |
| IgG1-14 (Example 3) | NGRKACLNPASPIVKKIIEKMLNSDKSN | 3 |
| IgG2b-1 (Example 3) | RCQCLQTLQGIHPKNIQSVNVK | 1 |
| Commercial antibody (Reference example 1) | SPGPHCAQTEVIATLK | 2 |

Example 4

Detection of Human CXCL1 by Sandwich ELISA Method Using Monoclonal Antibody IgG2b-1 and Monoclonal Antibody IgG1-10

Human CXCL1 was measured by a sandwich ELISA method using antibody IgG2b-1 revealed in Example 3 to specifically recognize the amino acid sequence region shown in SEQ ID NO: 1 and biotin-labeled antibody IgG1-10 revealed in Example 3 to specifically recognize the amino acid sequence region shown in SEQ ID NO: 3. IgG1-10 was biotinylated using Sulfo-NHS Biotin (PIERCE) according to the included protocols regarding details. First, a 10 µg/mL PBS solution of IgG2b-1 was prepared and then added to a 96-well polystyrene plate (Greiner Bio-One) at 100 µL per well, followed by overnight immobilization. On the next day, the solution was discarded, 200 µL of a 1% BSA-PBS solution (SIGMA) was poured and then the resultant was left to stand for 1 hour at room temperature. Subsequently, the plate was washed with PBS-T so that a plate on which the purified antibody had been immobilized was prepared. Next, an antigen solution was prepared by serial dilution of recombinant human CXCL1 with 1% BSA-PBS from 500 pg/mL to 7.8 pg/mL. The antigen solution was added to the plate at 100 µL per well, followed by 1 hour of reaction at room temperature. Next, the antigen solution within each well was discarded, the plate was washed with PBS-T, and then 100 µL of 1 µg/mL biotin-labeled IgG1-10 diluted with 1% BSA-PBS was allowed to react for 1 hour at room temperature. After washing, 100 µL of an avidin-HRP solution (R&D SYSTEMS) was allowed to react at room temperature for 30 minutes. Avidin-HRP was also diluted with 1% BSA-PBS. After washing with PBS-T, 100 µL of a TMB solution was added and reacted for 15 minutes. 100 µL of a 2N sulfuric acid solution was added to stop the reaction and then absorbance was measured at 450 nm. The results are shown in FIG. 1.

Example 5

Detection of Human CXCL1 by Sandwich ELISA Method Using Monoclonal Antibody IgG2b-1 and Monoclonal Antibody IgG1-14

Human CXCL1 was measured by a sandwich ELISA method using monoclonal antibody IgG2b-1 revealed in Example 3 to specifically recognize the amino acid sequence region shown in SEQ ID NO: 1 and biotin-labeled monoclonal antibody IgG1-14 revealed in Example 3 to specifically recognize the amino acid sequence region shown in SEQ ID NO: 3. Biotinylation of IgG1-14 and sandwich ELISA were carried out in a manner similar to Example 4. The results are shown in FIG. 1.

Example 6

Detection of Human CXCL1 by Sandwich ELISA Method Using Monoclonal Antibody IgG1-3 and Monoclonal Antibody IgG1-14

Human CXCL1 was measured by a sandwich ELISA method using antibody IgG1-3 revealed in Example 3 to specifically recognize the amino acid sequence region shown in SEQ ID NO: 2 and biotin-labeled antibody IgG1-14 revealed in Example 3 to specifically recognize the amino acid sequence region shown in SEQ ID NO: 3. Biotinylation of IgG1-14 and sandwich ELISA were carried out in a manner similar to that in Example 4. The results are shown in FIG. 1.

Comparative Example 1

Detection of Human CXCL1 by Sandwich ELISA Method Using Commercial Kit

Figure 4:
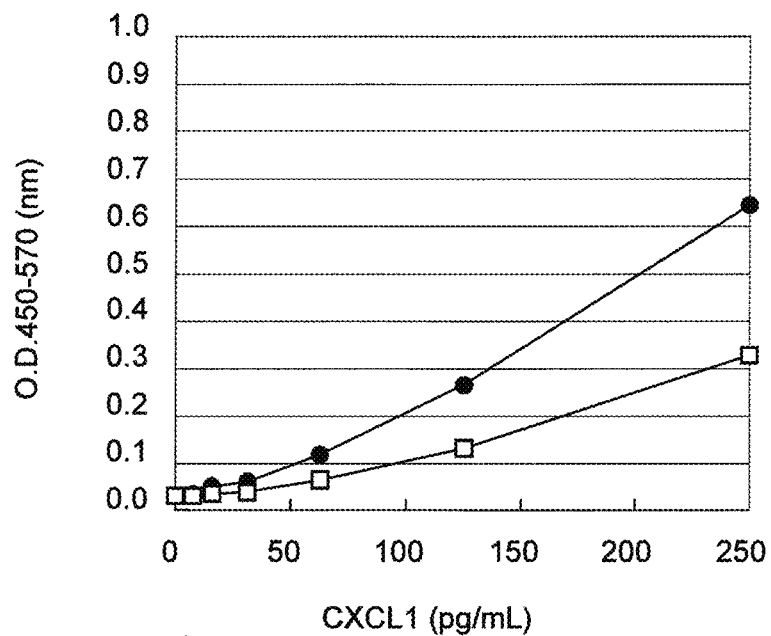
FIG. 4 is a graph showing the results of detecting human CXCL1 in a buffer by immobilizing a commercial antibody that specifically recognizes the amino acid sequence shown in SEQ ID NO: 2 and performing a sandwich ELISA method using the biotin-labeled antibody of the present invention recognizing the amino acid sequence shown in SEQ ID NO: 3 or a commercial biotin-labeled anti-human CXCL1 polyclonal antibody.
Figure 4:
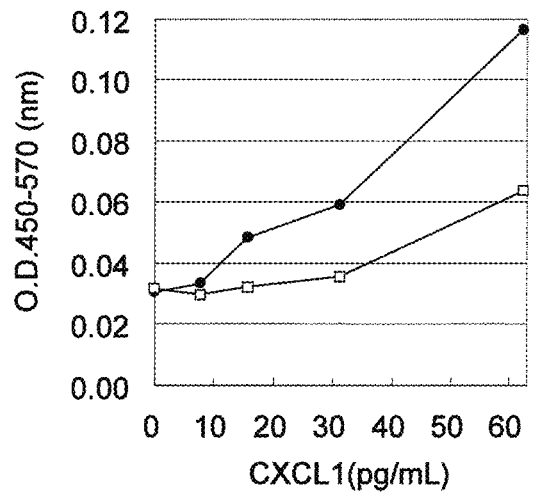
Figure 5:
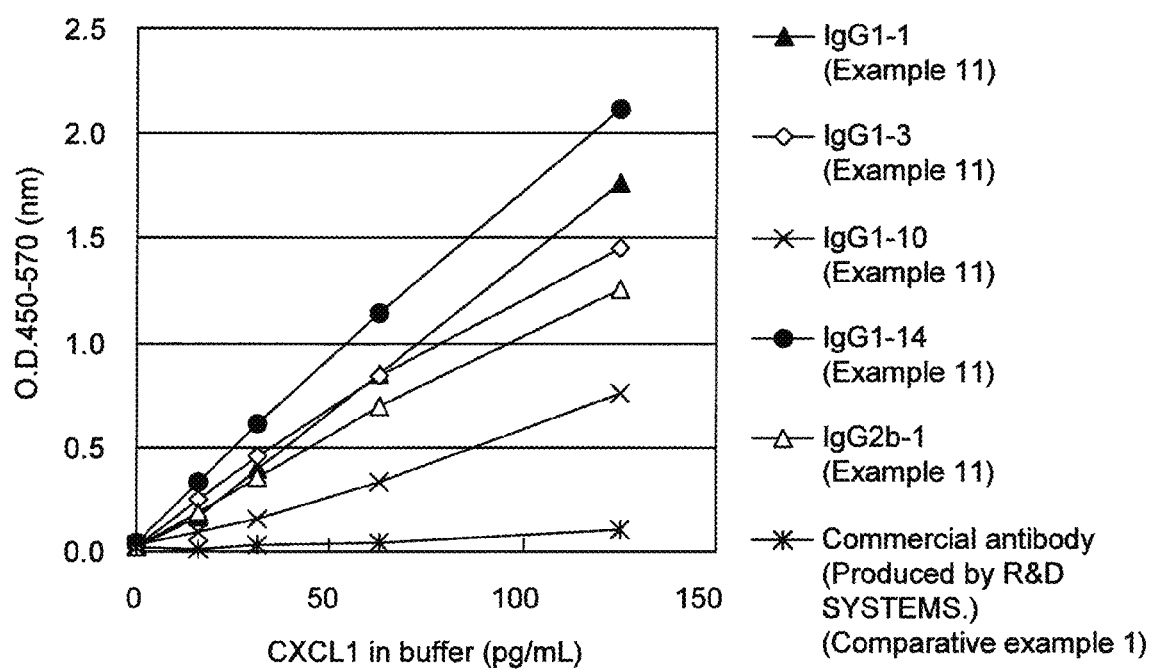
FIG. 5 is a graph showing the results of detecting human CXCL1 in a buffer by immobilizing the 5 types of antibody (IgG1-1, IgG1-3, IgG1-10, IgG1-14, and IgG2b-1) of the present invention and a commercial antibody and then carrying out a sandwich ELISA method using a biotin-labeled anti-human CXCL1 polyclonal antibody.

Recombinant human CXCL1 was measured using a commercial human CXCL1 detection kit, Human CXCL1/URO alpha DuoSet (R&D SYSTEMS). In this kit, an anti-human CXCL1 mouse monoclonal antibody (recognizing the amino acid sequence shown in SEQ ID NO: 2) was immobilized and a biotinylated (biotin-labeled) goat polyclonal antibody was used for detection. Immobilization was carried out onto a 96-well polystyrene plate (Greiner Bio-One). Experimental procedures were specifically carried out according to the attached protocols. The results are shown in FIGS. 1, 4, and 5.

From the results of Examples 4-6 and Comparative example 1, it was revealed that compared with the commercial human CXCL1 detection kit using a conventional method, the immunoassay of the present invention enabled detection of 7.8 pg/mL human CXCL1 and detection sensitivity of the immunoassay method of the present invention was enhanced.

Example 7

Detection of Human CXCL1 by Sandwich ELISA Method Using Monoclonal Antibody IgG2b-1 and Mixture of Monoclonal Antibodies IgG1-10 and IgG1-14

Figure 2:
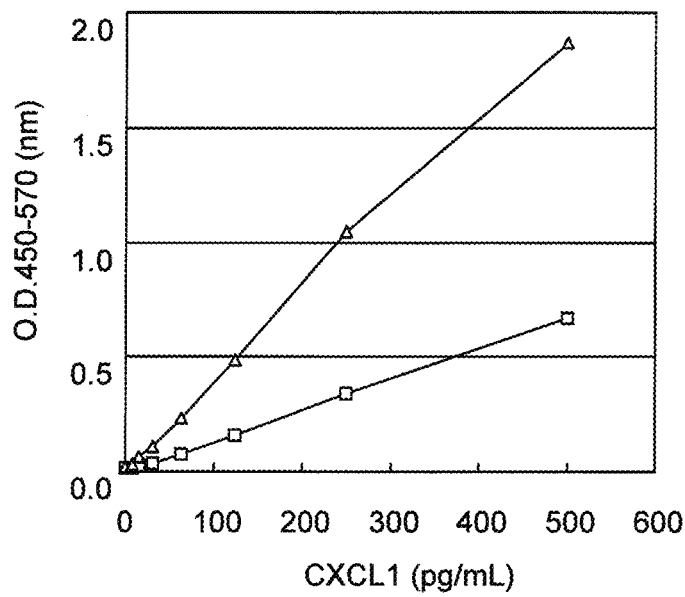
FIG. 2 shows sandwich ELISA method using as a labeled antibody a monoclonal antibody that specifically recognizes the amino acid sequence shown in SEQ ID NO: 3.
Figure 2:
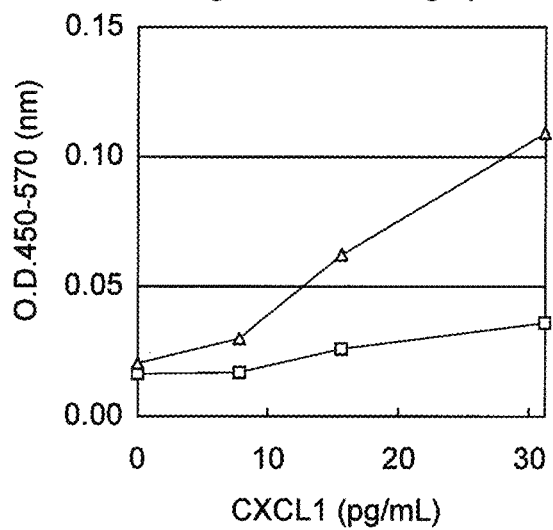

Human CXCL1 was measured by a sandwich ELISA method using antibody IgG2b-1 revealed in Example 3 to specifically recognize the amino acid sequence region shown in the same SEQ ID NO: 1 and biotin-labeled antibody IgG1-10 revealed in Example 3 to specifically recognize the amino acid sequence region shown in SEQ ID NO: 3 or a mixture of biotin-labeled IgG-10 and biotin-labeled IgG1-14. Biotinylation of the antibodies and sandwich ELISA were carried out in a manner similar to that in Example 4. The results are shown in FIG. 2.

By the use of the 2 types of monoclonal antibody specifically recognizing the same amino acid sequence region shown in SEQ ID NO: 3 as labeled antibodies, the signal intensity was more enhanced at each concentration than that in the case of a single type of antibody at the same concentration. It was revealed that the use of 2 types of antibody resulted in enhanced detection sensitivity for human CXCL1 to a degree higher than that in the case of using a single type of labeled antibody recognizing the same sequence.

Example 8

Detection of Human CXCL1 Added in Urine by Sandwich ELISA Method Using Monoclonal Antibody IgG2b-1 and Monoclonal Antibody IgG1-10 or IgG1-14

Figure 3:
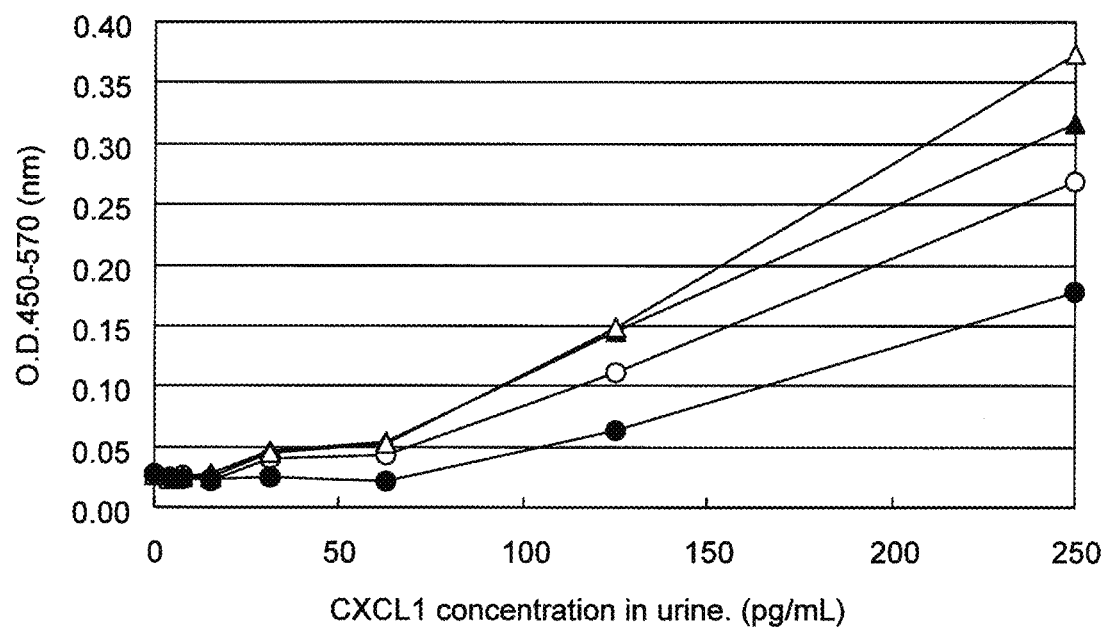
FIG. 3 shows sandwich ELISA method for detection of human CXCL1 in urine using a monoclonal antibody that specifically recognizes the amino acid sequence shown in SEQ ID NO: 1 or 2 and a monoclonal antibody that specifically recognizes the amino acid sequence shown in SEQ ID NO: 3.

Human CXCL1 added in urine was measured by a sandwich ELISA method using antibody IgG2b-1 revealed in Example 3 to specifically recognize the amino acid sequence region shown in SEQ ID NO: 1 and biotin-labeled antibody IgG1-10 or biotin-labeled IgG1-14 revealed in Example 3 to specifically recognize the amino acid sequence region shown in SEQ ID NO: 3. IgG1-10 and IgG1-14 were biotinylated using Sulfo-NHS Biotin (PIERCE) according to the included protocols regarding details. First, a 10 µg/mL PBS solution of IgG2b-1 was prepared and then added to a 96-well polystyrene plate (Greiner Bio-One) at 100 µL per well, followed by overnight immobilization. On the next day, the solution was discarded, 200 µL of a 1% BSA-PBS solution (SIGMA) was poured, and then the resultant was left to stand for 1 hour at room temperature. Subsequently, the plate was washed with PBS-T, so that a plate on which the purified antibody had been immobilized was prepared. Next, recombinant human CXCL1 was added into human urine collected on the day to a concentration of 250 pg/mL. Urine to which antigen had been added was serially diluted to 3.9 pg/mL with the same human urine and then the solution was added at 100 µL per well, followed by 1 hour of reaction at room temperature. Next, the antigen solution within each well was discarded and then the plate was washed with PBS-T. 100 µL of 1 µg/mL biotin-labeled IgG1-10 diluted using 1% BSA-PBS was allowed to react for 1 hour at room temperature. After washing, 100 µL of an avidin-HRP solution (R&D SYSTEMS) was allowed to react for 30 minutes at room temperature. Avidin-HRP was also diluted with 1% BSA-PBS. After washing with PBS-T, 100 µL of a TMB solution was added and reacted for 15 minutes. 100 µL of a 2N sulfuric acid solution was added to stop the reaction and then absorbance was measured at 450 nm. The results are shown in FIG. 3.

Example 9

Detection of Human CXCL1 Added in Urine by Sandwich Elisa Method Using Monoclonal Antibody IgG1-3 and Monoclonal Antibody IgG1-14

Human CXCL1 added in urine was measured by a sandwich ELISA method using antibody IgG1-3 revealed in Example 3 to specifically recognize the amino acid sequence region shown in SEQ ID NO: 2 and biotin-labeled antibody IgG1-14 revealed in Example 3 to specifically recognize the amino acid sequence region shown in SEQ ID NO: 3. Biotinylation of the antibody and sandwich ELISA were carried out in a manner similar to that in Example 8. The results are shown in FIG. 3.

Comparative Example 2

Detection of Human CXCL1 in Urine by Sandwich ELISA Method Using Commercial Kit

Recombinant human CXCL1 added in urine was measured using a commercial human CXCL1 detection kit, Human CXCL1/GRO alpha DuoSet (R&D SYSTEMS). Experimental procedures were specifically carried out according to the included protocols. A CXCL1 solution containing human urine was prepared in a manner similar to that in Example 8. The results are shown in FIG. 3.

From the results of Examples 8-9 and Comparative example 2, it was revealed that compared with the commercial human CXCL1 detection kit using the conventional method, the immunoassay method of the present invention enabled detection of 31.25 pg/mL human CXCL1 even in urine and enhanced the detection sensitivity.

Example 10

Detection of CXCL1 by Sandwich ELISA Method Using Monoclonal Antibody in Commercial Kit and Monoclonal Antibody IgG1-10

Human CXCL1 added to buffer was measured by a sandwich ELISA method using the mouse monoclonal antibody attached to a commercial kit, Human CXCL1/GRO alpha DuoSet (R&D SYSTEMS) and revealed in Example 3 to specifically recognize the amino acid sequence region shown in SEQ ID NO: 2, and biotin-labeled antibody IgG1-10 revealed in Example 3 to specifically recognize the amino acid sequence region shown in SEQ ID NO: 3. IgG1-10 was biotinylated using Sulfo-NHS Biotin (PIERCE) according to the included protocols regarding details. First, a 4 pg/mL PBS solution of the mouse monoclonal antibody attached to the commercial kit was prepared and then added to a 96-well polystyrene plate (Greiner Bio-One) at 100 µL per well, followed by overnight immobilization. On the next day, the solution was discarded, 200 µL of a 1% BSA-PBS solution (SIGMA) was poured, and then the resultant was left to stand for 1 hour at room temperature. Subsequently, the plate was washed with PBS-T, so that a plate on which the purified antibody had been immobilized was prepared. Next, an antigen solution was prepared by serial dilution of recombinant human CXCL1 with 1% BSA-PBS from 500 pg/mL to 7.8 pg/mL. The antigen solution was added at 100 µL per well and reacted for 1 hour at room temperature. Next, the antigen solution within each well was discarded and then the plate was washed with PBS-T. 100 µL of 1 µg/mL biotin-labeled IgG1-10 diluted with 1% BSA-PBS was allowed to react for 1 hour at room temperature. After washing, 100 µA of an avidin-HRP solution (R&D SYSTEMS) was allowed to react for 30 minutes at room temperature. Avidin-HRP was also diluted with 1% BSA-PBS. After washing with PBS-T, 100 µL of the TMB solution was added and reacted for 15 minutes. 100 µL of a 2N sulfuric acid solution was added to stop the reaction and then absorbance was measured at 450 nm. The results are shown in FIG. 4.

It was revealed that even when a monoclonal antibody included with a commercial kit had been used as an antibody recognizing SEQ ID NO: 2, 7.8 pg/mL human CXCL1 could be detected by a sandwich ELISA method using an antibody recognizing SEQ ID NO: 3 in combination with the aforementioned monoclonal antibody. Also, it was revealed that, according to a sandwich ELISA method using a combination of a monoclonal antibody included with a commercial kit and an antibody recognizing SEQ ID NO: 3, the result of detection sensitivity was enhanced than that using a commercial kit, that is, Comparative example 1.

Example 11

Detection of Human CXCL1 by ELISA Method Using Obtained Antibody

After preparation of a 10 µg/mL PBS solution for each of the 5 types of antibody IgG1-1, IgG1-3, IgG1-10, IgG1-14, and IgG2b-1 selected in Example 2, the PBS solution was added to a 96-well polystyrene plate (Greiner Bio-One) at 100 µL, per well, followed by overnight immobilization. On the next day, the solution was discarded, 200 µL of a 1% BSA-PBS solution (SIGMA) was poured, and then the resultant was left to stand for 1 hour at room temperature. Subsequently, the plate was washed with PBS-T, so that a plate on which the purified antibody had been immobilized was prepared. Next, an antigen solution was prepared by serial dilution of a recombinant human CXCL1 protein with 1% BSA-PBS from 125 pg/mL to 15 pg/mL. The antigen solution was added at 100 µL per well, followed by 1 hour of reaction at room temperature. Next the antigen solution within each well was discarded, the plate was washed with PBS-T, and then 100 µL of 50 ng/mL biotin-labeled anti-human CXCL1 polyclonal antibody (R&D SYSTEMS) diluted using 1% BSA-PBS was allowed to react for 1 hour at room temperature. After washing, 100 µL, of an avidin-HRP solution (R&D SYSTEMS) was allowed to react for 30 minutes at room temperature. Avidin-HRP was also diluted with 1% BSA-PBS. After washing with PBS-T, 100 µL of a TMB solution was added and reacted for 15 minutes. 100 µL of a 2N sulfuric acid solution was added to stop the reaction and then absorbance was measured at 450 nm. The results are shown in FIG. 5.

From the results of Examples 10 and 11 and Comparative example 1, it was revealed that all the IgG1-1, IgG1-3, IgG1-10, IgG1-14, and IgG2b-1 antibodies of the present invention exerted signal intensity stronger than that exerted by the commercial antibody and thus had high detection capability for human CXCL1.

Example 12

Detection of Human CXCL1 in Blood Plasma Using Obtained Antibody

Human CXCL1 dissolved in blood plasma was detected using the 5 types of antibody IgG1-1, IgG1-3, IgG1-10, IgG1-14, and IgG2b-1 selected in Example 2.

First, a 10 µg/mL PBS solution was prepared for each antibody and then added to a 96-well polystyrene plate (Greiner Bio-One) at 100 µL per well, followed by overnight immobilization. On the next day, the solution was discarded, 200 µL of a 1% BSA-PBS solution (SIGMA) diluted 4-fold was poured, and then the resultant was left to stand for 1 hour at room temperature. After washing with PBS-T, a plate on which the purified antibody had been immobilized was prepared.

Next, a blood plasma solution containing a 500 pg/mL recombinant human CXCL1 protein was prepared. A dilution series was prepared for the antigen blood plasma solution through serial dilution of the above-prepared solution using the same blood plasma to 125 pg/mL. Each antigen solution was added at 100 µL per well, a reaction took place for 1 hour at room temperature, and then the antigen solution was discarded, followed by washing with PBS-T.

Figure 6:
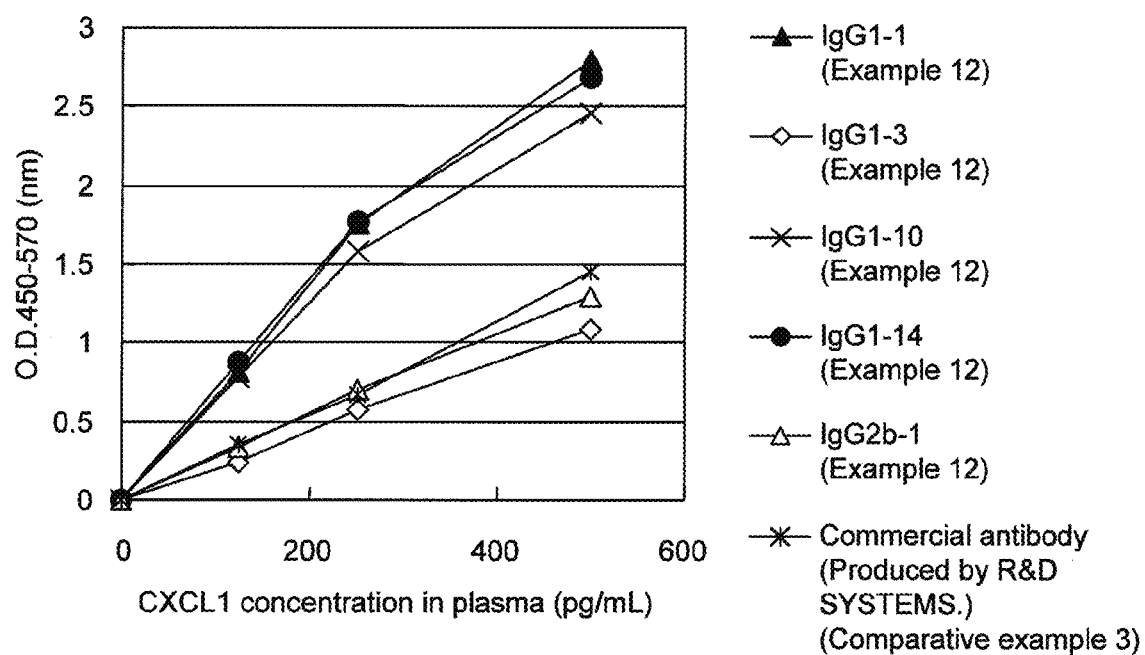
FIG. 6 is a graph showing the results of detecting human CXCL1 in blood plasma by immobilizing the 5 types of antibody of the present invention and a commercial antibody and then carrying out a sandwich ELISA method using a biotin-labeled anti-human CXCL1 polyclonal antibody.

Subsequently, 100 µL of 50 ng/mL biotin-labeled anti-human CXCL1 polyclonal antibody (R&D SYSTEMS) diluted with 1% BSA-PBS was added and reacted for 1 hour at room temperature. After washing, 100 µL of an avidin-HRP solution (R&D SYSTEMS) diluted with 1% BSA-PBS was allowed to react for 30 minutes at room temperature. After washing with PBS-T, 100 µL of a TMB solution was added and reacted for 15 minutes. 100 µL of a 2N sulfuric acid solution was added to stop the reaction and then absorbance was measured at 450 nm. The results are shown in FIG. 6.

Comparative Example 3

Detection of Human CXCL1 in Blood Plasma Using Commercial Antibody

Human CXCL1 dissolved in blood plasma was detected using MAB275 (R&D SYSTEMS) that was a commercial anti-human CXCL1 monoclonal antibody. A 10 µg/mL MAB275 solution diluted with PBS was prepared and then added to a 96-well polystyrene plate (Greiner Bio-One) at 100 µL per well, followed by overnight immobilization. Subsequent procedures were carried out by a method similar to that in Example 6. The results are shown in FIG. 6.

From the results of Example 12 and Comparative example 3, it was revealed that human CXCL1 dissolved in blood plasma can also be detected using the 5 types of antibody of the present invention.

Example 13

Detection of Human CXCL1 in Urine Using Obtained Antibody

Human CXCL1 dissolved in urine was detected using the 5 types of antibody, IgG1-1, IgG1-3, IgG1-10, IgG1-14, and IgG2b-1 selected in Example 2.

First, a 10 µg/mL PBS solution was prepared for each antibody and then added to a 96-well polystyrene plate (Greiner Bio-One) at 100 µL per well, followed by overnight immobilization. On the next day, the solution was discarded, 200 µL of a 1% BSA-PBS solution (SIGMA) diluted 4-fold was poured, and then the resultant was left to stand for 1 hour at room temperature. After washing with PBS-T, a plate on which the purified antibody had been immobilized, was prepared.

Next, a urine solution containing a recombinant human CXCL1 protein at 500 pg/mL was prepared. A dilution series was prepared for the antigen urine solution through serial dilution of the antigen urine solution with the same urine to 125 pg/mL. Each antigen urine solution was added at 100 µL per well, followed by 1 hour of reaction at room temperature. The antigen solution was discarded and then the wells were washed with PBS-T.

Figure 7:
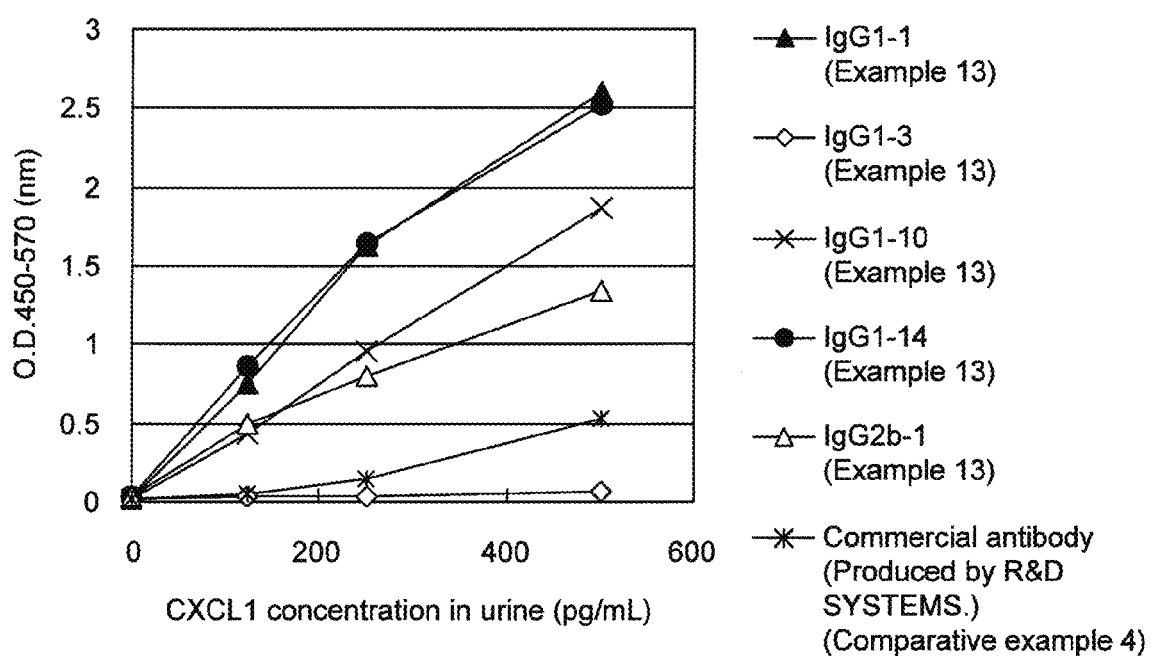
FIG. 7 is a graph showing the results of detecting human CXCL1 in urine by immobilizing the 5 types of antibody of the present invention and a commercial antibody and then carrying out a sandwich ELISA method using a biotin-labeled anti-human CXCL1 polyclonal antibody.

Subsequently, 100 µL of 50 ng/mL biotin-labeled anti-human CXCL1 polyclonal antibody (R&D SYSTEMS) diluted with 1% BSA-PBS was added and reacted for 1 hour at room temperature. After washing, 100 µL of an avidin-HRP solution (R&D SYSTEMS) diluted with 1% BSA-PBS was allowed to react for 30 minutes at room temperature. After washing with PBS-T, 100 µL of a TMB solution was poured and reacted for 15 minutes. 100 µL of a 2N sulfuric acid solution was added to stop the reaction and then absorbance was measured at 450 nm. The results are shown in FIG. 7.

Comparative Example 4

Detection of Human CXCL1 in Urine Using Commercial Antibody

Human CXCL1 dissolved in urine was detected using a commercial anti-human CXCL1 monoclonal antibody, MAB275 (R&D SYSTEMS). A 10 µg/mL MAB275 solution diluted with PBS was prepared and then added to a 96-well polystyrene plate (Greiner Bio-One) at 100 µL per well, followed by overnight immobilization. Subsequent procedures were carried out by a method similar to that in Example 13. The results are shown in FIG. 7.

From the results of Example 13 and Comparative example 4, it was revealed that human CXCL1 dissolved in urine could also be detected using the 4 out of the 5 types of antibody of the present invention.

Example 14

Experiment (1) for Measuring Activity of Neutralizing the Invasion Ability of Bladder Cancer Cells Using Monoclonal Antibodies, IgG1-1, IgG1-3, IgG1-10, IgG1-14, and IgG2b-1

The 5 types of antibody, IgG1-1, IgG1-3, IgG1-10, IgG1-14, and IgG2b-1 selected in Example 2 were subjected to measurement of neutralization activity to suppress the invasion ability of bladder cancer cells.

First, T24 cells, which is bladder cancer cells, were inoculated to RPMI1640 medium supplemented with 10% FCS and 12.5 mM HEPES at $1.0 \times 10^5$ cells/mL, followed by 40 hours of pre-culture. After the pre-culture, cells were collected and then mixed with each antibody to prepare cell solutions. Each cell solution was subjected to measurement of invasion ability using Matrigel Invasion Chamber (BD Falcon) according to the included protocols regarding details. 100 µL of a $2.0 \times 10^5$ cells/mL PBS suspension and each antibody were added to a final concentration of 10 µg/mL into Matrigel Invasion Chamber. At 37° C. under 5% $CO_2$, invasion culture was carried out for 5 hours. After culture, the lower part of the chamber was stained with a Diff-Quick reagent (Sysmex) and then the number of bladder cancer cells that had invaded to the lower part of the chamber was counted. Cells within 5 visual fields each having a size of 0.8 cm×0.6 cm were counted using a microscope and then the results were summed up. Measurement was carried out twice (n=2) for each case. The total values were averaged and shown in FIG. 8.

Comparative Example 5

Figure 8:
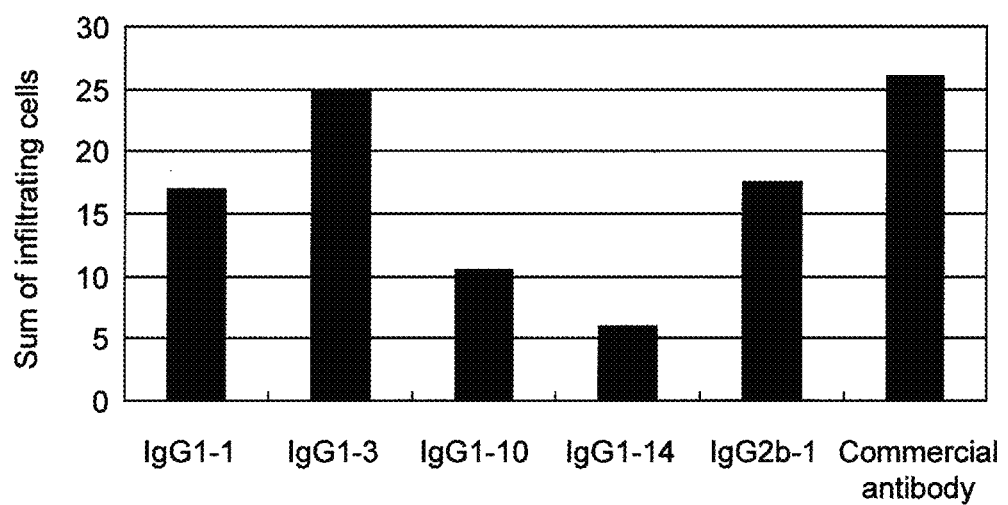
FIG. 8 is graph (1) showing the bladder cancer cell invasion-suppressing capability of the 5 types of antibody of the present invention and a commercial antibody.

Experiment for Measuring Activity of Neutralizing the Invasion Ability of Bladder Cancer Cells Using Commercial Antibody A commercial anti-human CXCL1 monoclonal antibody, MAB275 (R&D SYSTEMS), was subjected to measurement of the neutralization activity to suppress the invasion ability of bladder cancer cells. Measurement was carried out by a method similar to that in Example 14. The results are shown in FIG. 8.

As revealed by Example 14 and Comparative example 5, the 5 antibodies of the present invention exerted neutralization activity equivalent to or higher than that of the commercial antibody and particularly IgG1-1, IgG1-10, IgG1-14, and IgG2b-1 exerted high activity.

Example 15

Experiment (2) for Measuring Activity of Neutralizing the Invasion Ability of Bladder Cancer Cells Using Monoclonal Antibodies IgG1-3, IgG1-10, IgG1-14, and IgG2b-1

The 4 (IgG1-3, IgG1-10, IgG1-14, and IgG2b-1) out of the 5 types of antibody selected in Example 2 were subjected to measurement of neutralization activity to suppress the invasion ability of bladder cancer cells. Incidentally, unlike Example 14, antibodies were not mixed immediately before measurement of invasion ability, but mixed at the stage of pre-culture.

First, T24 cells, which is bladder cancer cells, were inoculated into RPMI1640 medium supplemented with 10% FCS and 12.5 mM HEPES at $1.0 \times 10^5$ cells/mL and then each antibody was added to a final concentration of 10 μg/mL, followed by 40 hours of culture. After culture, cells were collected and then mixed with each antibody so as to prepare cell solutions. Each cell solution was subjected to measurement of invasion ability using Matrigel Invasion Chamber (BD Falcon). Thereafter, an experiment similar to that in Example 14 was conducted and only the time for invasion culture was changed to 6.5 hours. The number of cells that had invaded was counted in a manner similar to that in Example 14. The results are shown in FIG. 8.

Comparative Example 6

Figure 9:
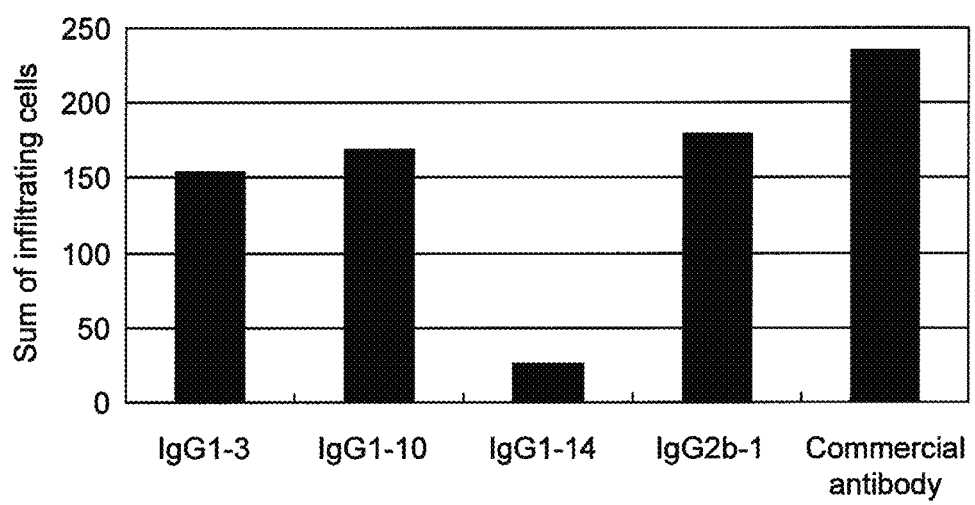
FIG. 9 is a graph (2) showing bladder cancer cell invasion-suppressing capability of the 4 types of antibody of the present invention and a commercial antibody.

Experiment 2 for Measuring Activity of Neutralizing the Invasion Ability of Bladder Cancer Cells Using Commercial Antibody MAB275 (R&D SYSTEMS) that was a commercial anti-human CXCL1 monoclonal antibody was subjected to measurement of neutralization activity to suppress the invasion ability of bladder cancer cells. Unlike Comparative example 5, the antibody was not mixed immediately before measurement of invasion ability, but mixed at the stage of pre-culture. This was carried out by a method similar to that in Example 15. The results are shown in FIG. 9.

From the results of Example 15 and Comparative example 6, all the 4 antibodies encompassed in the present invention exerted neutralization activity higher than that of the commercial antibody.

INDUSTRIAL APPLICABILITY

According to the present invention, the concentration of human CXCL1 can be measured with higher sensitivity by the method of the present invention than the conventional methods. Thus the present invention is applicable to detection of cancer such as urothelial cancer.

The invention claimed is:

1. An immunoassay method for measuring a human CXCL1 protein comprising:

contacting the human CXCL1 protein or an antibody-binding fragment thereof in a sample with at least one immobilized first monoclonal antibody or at least one immobilized first antigen-binding fragment thereof, wherein the immobilized first monoclonal antibody or the immobilized first antigen-binding fragment thereof has specificity for at least one epitope region of human CXCL1 protein, wherein the human CXCL1 protein forms a complex with the immobilized first monoclonal antibody or the immobilized first antigen-binding fragment thereof, adding at least one labeled anti-human CXCL1 monoclonal antibody or at least one labeled antigen-binding fragment thereof, wherein the labeled anti-human CXCL1 monoclonal antibody or the labeled antigen-binding fragment thereof specifically binds an epitope region different from and non-overlapping with that or those bound by the at least one immobilized first antibody or the at least one immobilized first antigen binding fragment thereof and specifically binds with the CXCL1 protein bound in the complex with the at least one immobilized first monoclonal antibody or the at least one immobilized first antigen-binding fragment thereof, and detecting an amount of signal from the label of the labeled anti-human CXCL1 monoclonal antibody, or the labeled antigen-binding fragment(s) thereof, specifically bound to the antigen-antibody complex(es) as indicative of a level of the human CXCL1 or the antibody-binding fragment thereof in the sample, wherein the immobilized first monoclonal antibody and the labeled anti-human CXCL1 monoclonal antibody are selected from the group consisting of the following (a) to (e):

(a) an isolated antibody which specifically recognizes the amino acid sequence region shown in SEQ ID NO: 3 that is partial sequence of the amino acid sequence comprising the human CXCL 1 protein, wherein:

in its light chains,
CDR1 comprises the amino acid sequence shown in SEQ ID NO: 4,
CDR2 comprises the amino acid sequence shown in SEQ ID NO: 5, and
CDR3 comprises the amino acid sequence shown in SEQ ID NO: 6;

in its heavy chains,
CDR1 comprises the amino acid sequence shown in SEQ ID NO: 7,
CDR2 comprises the amino acid sequence shown in SEQ ID NO: 8, and
CDR3 comprises the amino acid sequence shown in SEQ ID NO: 9;

(b) an isolated antibody which specifically recognizes the amino acid sequence region shown in SEQ ID NO: 1 that is partial sequence of the amino acid sequence comprising the human CXCL1 protein, wherein:

in its light chains,
CDR1 comprises the amino acid sequence shown in SEQ ID NO: 12,
CDR2 comprises the amino acid sequence shown in SEQ ID NO: 13, and
CDR3 comprises the amino acid sequence shown in SEQ ID NO: 14;

in its heavy chains,
CDR1 comprises the amino acid sequence shown in SEQ ID NO: 15,
CDR2 comprises the amino acid sequence shown in SEQ ID NO: 16, and CDR3 comprises the amino acid sequence shown in SEQ ID NO: 17;
(c) an isolated antibody which specifically recognizes the amino acid sequence region shown in SEQ ID NO: 3, wherein:
in its light chains,
CDR1 comprises the amino acid sequence shown in SEQ ID NO: 20,
CDR2 comprises the amino acid sequence shown in SEQ ID NO: 21, and
CDR3 comprises the amino acid sequence shown in SEQ ID NO: 22;
in its heavy chains,
CDR1 comprises the amino acid sequence shown in SEQ ID NO: 23,
CDR2 comprises the amino acid sequence shown in SEQ ID NO: 24, and
CDR3 comprises the amino acid sequence shown in SEQ ID NO: 25;
(d) an isolated antibody which specifically recognizes the amino acid sequence region shown in SEQ ID NO: 2 that is partial sequence of the amino acid sequence comprising the human CXCL1 protein, wherein:
in its light chains,
CDR1 comprises the amino acid sequence shown in SEQ ID NO: 28,
CDR2 comprises the amino acid sequence shown in SEQ ID NO: 29, and
CDR3 comprises the amino acid sequence shown in SEQ ID NO: 30;
in its heavy chains,
CDR1 comprises the amino acid sequence shown in SEQ ID NO: 31,
CDR2 comprises the amino acid sequence shown in SEQ ID NO: 32, and
CDR3 comprises the amino acid sequence shown in SEQ ID NO: 33; and
(e) an isolated antibody which specifically recognizes the amino acid sequence region shown in SEQ ID NO: 3, wherein:
in its light chains,
CDR1 comprises the amino acid sequence shown in SEQ ID NO: 36,
CDR2 comprises the amino acid sequence shown in SEQ ID NO: 37, and
CDR3 comprises the amino acid sequence shown in SEQ ID NO: 38;
in its heavy chains,
CDR1 comprises the amino acid sequence shown in SEQ ID NO: 39,
CDR2 comprises the amino acid sequence shown in SEQ ID NO: 40, and
CDR3 comprises the amino acid sequence shown in SEQ ID NO: 41.

2. The immunoassay method for a human CXCL1 protein according to claim 1, in which the labeled anti-human CXCL1 monoclonal antibody or the labeled antigen-binding fragment thereof specifically recognizes the amino acid sequence region shown in SEQ ID NO: 3.

3. The immunoassay method for a human CXCL1 protein according to claim 1 or 2, in which the immobilized anti-human CXCL1 monoclonal antibody or the immobilized antigen-binding fragment thereof specifically recognizes the amino acid sequence region shown in SEQ ID NO: 1 and the labeled anti-human CXCL1 monoclonal antibody or the labeled antigen-binding fragment thereof specifically recognizes the amino acid sequence region shown in SEQ ID NO: 3.

4. The immunoassay method for a human CXCL1 protein according to claim 1 or 2, in which the immobilized anti-human CXCL1 monoclonal antibody or the immobilized antigen-binding fragment thereof specifically recognizes the amino acid sequence region shown in SEQ ID NO: 2 and the labeled anti-human CXCL1 monoclonal antibody or the labeled antigen-binding fragment thereof specifically recognizes the amino acid sequence region shown in SEQ ID NO: 3.

5. The immunoassay method for a human CXCL1 protein according to claim 1, wherein the sample is a tissue collected after an operation, blood, serum, blood plasma, urine, spinal fluid, saliva, lymph fluid, lacrimal fluid, or seminal fluid.

6. A purified anti-human CXCLI monoclonal antibody or a purified antigen-binding fragment thereof, which specifically recognizes the amino acid sequence region shown in SEQ ID NO: 3, wherein:
in its light chains, CDR1 comprises the amino acid sequence shown in SEQ ID NO: 4, CDR2 comprises the amino acid sequence shown in SEQ ID NO: 5, and CDR3 comprises the amino acid sequence shown in SEQ ID NO: 6;
in its heavy chains, CDR1 comprises the amino acid sequence shown in SEQ ID NO: 7, CDR2 comprises the amino acid sequence shown in SEQ ID NO: 8, and CDR3 comprises the amino acid sequence shown in SEQ ID NO: 9.

7. The purified anti-human CXCL1 monoclonal antibody or an antigen-binding fragment thereof according to claim 6, containing the amino acid sequence shown in SEQ ID NO: 10 in a light-chain variable region and the amino acid sequence shown in SEQ ID NO: 11 in a heavy-chain variable region.

8. A purified anti-human CXCL1 monoclonal antibody or a purified antigen-binding fragment thereof, which specifically recognizes the amino acid sequence region shown in SEQ ID NO: 1, wherein:
in its light chains, CDR1 comprises the amino acid sequence shown in SEQ ID NO: 12, CDR2 comprises the amino acid sequence shown in SEQ ID NO: 13, and CDR3 comprises the amino acid sequence shown in SEQ ID NO: 14; and
in its heavy chains, CDR1 comprises the amino acid sequence shown in SEQ ID NO: 15, CDR2 comprises the amino acid sequence shown in SEQ ID NO: 16, and CDR3 comprises the amino acid sequence shown in SEQ ID NO: 17.

9. The purified anti-human CXCL1 monoclonal antibody or a purified antigen-binding fragment thereof according to claim 8, containing the amino acid sequence shown in SEQ ID NO: 18 in a light-chain variable region and the amino acid sequence shown in SEQ ID NO: 19 in a heavy-chain variable region.

10. A purified anti-human CXCL1 monoclonal antibody or a purified antigen-binding fragment thereof, which specifically recognizes the amino acid sequence region shown in SEQ ID NO: 3, wherein:
in its light chains, CDR1 comprises the amino acid sequence shown in SEQ ID NO: 20, CDR2 comprises the amino acid sequence shown in SEQ ID NO: 21, and CDR3 comprises the amino acid sequence shown in SEQ ID NO: 22; and
in its heavy chains, CDR1 comprises the amino acid sequence shown in SEQ ID NO: 23, CDR2 comprises the amino acid sequence shown in SEQ ID NO: 24, and CDR3 comprises the amino acid sequence shown in SEQ ID NO: 25.

11. The purified anti-human CXCL1 monoclonal antibody or a purified antigen-binding fragment thereof according to claim 10, containing the amino acid sequence shown in SEQ ID NO: 26 in a light-chain variable region and the amino acid sequence shown in SEQ ID NO 27 in a heavy-chain variable region.

12. A purified anti-human CXCL1 monoclonal antibody or a purified antigen-binding fragment thereof, which specifically recognizes the amino acid sequence region shown in SEQ ID NO: 2, wherein:
   in its light chains, CDR1 comprises the amino acid sequence shown in SEQ ID NO: 28, CDR2 comprises the amino acid sequence shown in SEQ ID NO: 29, and CDR3 comprises the amino acid sequence shown in SEQ ID NO: 30; and
   in its heavy chains, CDR1 comprises the amino acid sequence shown in SEQ ID NO: 31, CDR2 comprises the amino acid sequence shown in SEQ ID NO: 32, and CDR3 comprises the amino acid sequence shown in SEQ ID NO: 33.

13. The purified anti-human CXCL1 monoclonal antibody or a purified antigen-binding fragment thereof according to claim 12, containing the amino acid sequence shown in SEQ ID NO: 34 in a light-chain variable region and the amino acid sequence shown in SEQ ID NO: 35 in a heavy-chain variable region.

14. A purified anti-human CXCL1 monoclonal antibody or a purified antigen-binding fragment thereof, which specifically recognizes the amino acid sequence region shown in SEQ ID NO: 3, wherein:
   in its light chains, CDR1 comprises the amino acid sequence shown in SEQ ID NO: 36, CDR2 comprises the amino acid sequence shown in SEQ ID NO: 37, and CDR3 comprises the amino acid sequence shown in SEQ ID NO: 38; and
   in its heavy chains, CDR1 comprises the amino acid sequence shown in SEQ ID NO: 39, CDR2 comprises the amino acid sequence shown in SEQ ID NO: 40, and CDR3 comprises the amino acid sequence shown in SEQ ID NO: 41.

15. The purified anti-human CXCL1 monoclonal antibody or a purified antigen-binding fragment thereof according to claim 14, containing the amino acid sequence shown in SEQ ID NO: 42 in a light-chain variable region and the amino acid sequence shown in SEQ ID NO: 43 in a heavy-chain variable region.

* * * * *

SEQUENCE LISTING

```
<160> NUMBER OF SEQ ID NOS: 45

<210> SEQ ID NO 1
<211> LENGTH: 22
<212> TYPE: PRT
<213> ORGANISM: Artificial Sequence
<220> FEATURE:
<223> OTHER INFORMATION: Synthetic epitope

<400> SEQUENCE: 1

Arg Cys Gln Cys Leu Gln Thr Leu Gln Gly Ile His Pro Lys Asn Ile
1               5                   10                  15

Gln Ser Val Asn Val Lys
            20

<210> SEQ ID NO 2
<211> LENGTH: 16
<212> TYPE: PRT
<213> ORGANISM: Artificial Sequence
<220> FEATURE:
<223> OTHER INFORMATION: Synthetic epitope

<400> SEQUENCE: 2

Ser Pro Gly Pro His Cys Ala Gln Thr Glu Val Ile Ala Thr Leu Lys
1               5                   10                  15

<210> SEQ ID NO 3
<211> LENGTH: 28
<212> TYPE: PRT
<213> ORGANISM: Artificial Sequence
<220> FEATURE:
<223> OTHER INFORMATION: Synthetic epitope

<400> SEQUENCE: 3

Asn Gly Arg Lys Ala Cys Leu Asn Pro Ala Ser Pro Ile Val Lys Lys
1               5                   10                  15

Ile Ile Glu Lys Met Leu Asn Ser Asp Lys Ser Asn
            20                  25
```

```
<210> SEQ ID NO 4
<211> LENGTH: 15
<212> TYPE: PRT
<213> ORGANISM: Artificial Sequence
<220> FEATURE:
<223> OTHER INFORMATION: Synthetic variable region sequence

<400> SEQUENCE: 4

Arg Ala Ser Glu Ser Val Asp Ser Phe Gly Asp Ser Leu Met His
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: Synthetic variable region sequence

<400> SEQUENCE: 5

Arg Ala Ser Asn Leu Glu Pro
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic variable region sequence

<400> SEQUENCE: 6

Gln Gln Ser Asn Glu Asp Pro Phe Thr
1               5

<210> SEQ ID NO 7
<211> LENGTH: 10
<212> TYPE: PRT
<213> ORGANISM: Artificial Sequence
<220> FEATURE:
<223> OTHER INFORMATION: Synthetic variable region sequence

<400> SEQUENCE: 7

Gly Phe Thr Phe Asp Thr Tyr Ala Met Asn
1               5                   10

<210> SEQ ID NO 8
<211> LENGTH: 19
<212> TYPE: PRT
<213> ORGANISM: Artificial Sequence
<220> FEATURE:
<223> OTHER INFORMATION: Synthetic variable region sequence

<400> SEQUENCE: 8

Arg Ile Arg Ser Lys Ser Tyr Asn Tyr Ala Thr Phe Tyr Ala Asp Ser
1               5                   10                  15

Val Lys Ala

<210> SEQ ID NO 9
<211> LENGTH: 5
<212> TYPE: PRT
<213> ORGANISM: Artificial Sequence
<220> FEATURE:
<223> OTHER INFORMATION: Synthetic variable region sequence

<400> SEQUENCE: 9

Gly Gly Phe Ala Asp
```

```
<210> SEQ ID NO 10
<211> LENGTH: 151
<212> TYPE: PRT
<213> ORGANISM: Artificial Sequence
<220> FEATURE:
<223> OTHER INFORMATION: Synthetic variable region sequence

<400> SEQUENCE: 10

Glu Phe Met Glu Thr Asp Thr Leu Leu Leu Trp Val Leu Leu Leu Trp
1               5                   10                  15

Val Pro Gly Ser Thr Gly Asp Ile Val Leu Thr Gln Ser Pro Val Ser
            20                  25                  30

Leu Ala Val Ser Leu Gly Gln Arg Ala Thr Ile Ser Cys Arg Ala Ser
        35                  40                  45

Glu Ser Val Asp Ser Phe Gly Asp Ser Leu Met His Trp Tyr Gln Gln
    50                  55                  60

Lys Pro Gly Gln Pro Pro Lys Leu Leu Ile Tyr Arg Ala Ser Asn Leu
65                  70                  75                  80

Glu Pro Gly Ile Pro Ala Arg Phe Ser Gly Ser Gly Ser Arg Thr Asp
                85                  90                  95

Phe Thr Leu Thr Ile Asn Pro Val Glu Ala Asp Asp Val Ala Thr Tyr
            100                 105                 110

Tyr Cys Gln Gln Ser Asn Glu Asp Pro Phe Thr Phe Gly Gly Gly Thr
        115                 120                 125

Lys Leu Glu Ile Lys Arg Ala Asp Ala Ala Pro Thr Val Ser Ile Phe
    130                 135                 140

Pro Pro Ser Ser Lys Leu Gly
145                 150

<210> SEQ ID NO 11
<211> LENGTH: 153
<212> TYPE: PRT
<213> ORGANISM: Artificial Sequence
<220> FEATURE:
<223> OTHER INFORMATION: Synthetic variable region sequence

<400> SEQUENCE: 11

Glu Phe Met Glu Leu Gly Leu Ser Trp Val Phe Phe Val Val Phe Tyr
1               5                   10                  15

Gln Gly Val His Cys Glu Val Gln Leu Val Glu Ser Gly Gly Gly Leu
            20                  25                  30

Val Gln Pro Lys Gly Ser Leu Lys Leu Ser Cys Ala Ala Ser Gly Phe
        35                  40                  45

Thr Phe Asp Thr Tyr Ala Met Asn Trp Phe Arg Gln Ala Pro Gly Lys
    50                  55                  60

Gly Leu Glu Trp Val Thr Arg Ile Arg Ser Lys Ser Tyr Asn Tyr Ala
65                  70                  75                  80

Thr Phe Tyr Ala Asp Ser Val Lys Ala Arg Phe Thr Ile Ser Arg Asp
                85                  90                  95

Asp Ser Gln Asn Met Leu Tyr Leu Gln Met Asn Asn Leu Lys Thr Glu
            100                 105                 110

Asp Thr Ala Met Tyr Tyr Cys Val Arg Gly Gly Phe Ala Asp Trp Gly
        115                 120                 125

Gln Gly Thr Leu Val Thr Val Ser Pro Ala Lys Thr Thr Pro Pro Ser
    130                 135                 140
```

```
Val Tyr Pro Leu Val Pro Gly Ser Leu
145                 150

<210> SEQ ID NO 12
<211> LENGTH: 15
<212> TYPE: PRT
<213> ORGANISM: Artificial Sequence
<220> FEATURE:
<223> OTHER INFORMATION: Synthetic variable region sequence

<400> SEQUENCE: 12

Lys Ala Ser Gln Ser Val Asp Tyr Asp Gly Asp Ser Tyr Met Asn
1               5                   10                  15

<210> SEQ ID NO 13
<211> LENGTH: 7
<212> TYPE: PRT
<213> ORGANISM: Artificial Sequence
<220> FEATURE:
<223> OTHER INFORMATION: Synthetic variable region sequence

<400> SEQUENCE: 13

Ala Ala Ser Asn Leu Glu Ser
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic variable region sequence

<400> SEQUENCE: 14

Gln Gln Ser Asn Glu Asp Pro Leu Thr
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic variable region sequence

<400> SEQUENCE: 15

Asn Tyr Trp Ile Asn
1               5

<210> SEQ ID NO 16
<211> LENGTH: 17
<212> TYPE: PRT
<213> ORGANISM: Artificial Sequence
<220> FEATURE:
<223> OTHER INFORMATION: Synthetic variable region sequence

<400> SEQUENCE: 16

Asp Ile Tyr Pro Gly Gly Gly Tyr Asn Thr Tyr Asn Glu Lys Phe Lys
1               5                   10                  15

Gly

<210> SEQ ID NO 17
<211> LENGTH: 11
<212> TYPE: PRT
<213> ORGANISM: Artificial Sequence
<220> FEATURE:
<223> OTHER INFORMATION: Synthetic variable region sequence

<400> SEQUENCE: 17
```

```
Gly Gly Tyr Gly Arg Glu Gly Ala Val Asp Tyr
1               5                   10
```

<210> SEQ ID NO 18
<211> LENGTH: 150
<212> TYPE: PRT
<213> ORGANISM: Artificial Sequence
<220> FEATURE:
<223> OTHER INFORMATION: Synthetic variable region sequence

<400> SEQUENCE: 18

```
Glu Phe Met Glu Thr Asp Thr Leu Leu Leu Trp Val Leu Leu Leu Trp
1               5                   10                  15

Val Pro Gly Ser Thr Gly Asp Ile Val Leu Thr Gln Ser Pro Ala Ser
            20                  25                  30

Leu Ala Val Ser Leu Gly Gln Arg Ala Thr Ile Ser Cys Lys Ala Ser
        35                  40                  45

Gln Ser Val Asp Tyr Asp Gly Asp Ser Tyr Met Asn Trp Tyr Gln Gln
50                  55                  60

Lys Pro Gly Gln Pro Pro Lys Leu Leu Ile Tyr Ala Ala Ser Asn Leu
65                  70                  75                  80

Glu Ser Gly Ile Pro Ala Arg Phe Ser Gly Ser Gly Ser Gly Thr Asp
                85                  90                  95

Phe Thr Leu Asn Ile His Pro Val Glu Glu Asp Ala Ala Thr Tyr
            100                 105                 110

Tyr Cys Gln Gln Ser Asn Glu Asp Pro Leu Thr Phe Gly Ala Gly Thr
        115                 120                 125

Lys Leu Glu Leu Lys Arg Ala Asp Ala Ala Pro Thr Val Ser Ile Phe
130                 135                 140

His His Pro Val Ser Leu
145                 150
```

<210> SEQ ID NO 19
<211> LENGTH: 157
<212> TYPE: PRT
<213> ORGANISM: Artificial Sequence
<220> FEATURE:
<223> OTHER INFORMATION: Synthetic variable region sequence

<400> SEQUENCE: 19

```
Glu Phe Met Glu Cys Ser Trp Val Ile Leu Phe Leu Leu Ser Val Thr
1               5                   10                  15

Ala Gly Val His Ser Gln Val Gln Leu Gln Gln Ser Gly Ala Glu Leu
            20                  25                  30

Val Arg Pro Gly Thr Ser Val Lys Met Ser Cys Lys Ala Ala Gly Tyr
        35                  40                  45

Thr Phe Thr Asn Tyr Trp Ile Asn Trp Val Lys Gln Arg Pro Gly His
50                  55                  60

Gly Leu Glu Trp Ile Gly Asp Ile Tyr Pro Gly Gly Tyr Asn Thr
65                  70                  75                  80

Tyr Asn Glu Lys Phe Lys Gly Lys Ala Thr Leu Thr Ala Asp Thr Ser
                85                  90                  95

Ser Ser Thr Ala Tyr Met Gln Leu Ser Ser Leu Thr Ser Glu Asp Ser
            100                 105                 110

Ala Ile Tyr Tyr Cys Ala Lys Gly Gly Tyr Gly Arg Glu Gly Ala Val
        115                 120                 125

Asp Tyr Trp Gly Gln Gly Thr Ser Val Thr Val Ser Ser Ala Lys Thr
```

```
            130                 135                 140
Thr Pro Pro Ser Val Tyr Pro Leu Ala Pro Gly Ser Leu
145                 150                 155

<210> SEQ ID NO 20
<211> LENGTH: 15
<212> TYPE: PRT
<213> ORGANISM: Artificial Sequence
<220> FEATURE:
<223> OTHER INFORMATION: Synthetic variable region sequence

<400> SEQUENCE: 20

Arg Ala Ser Glu Ser Val Asp Phe Tyr Gly Asn Arg Leu Leu His
1               5                   10                  15

<210> SEQ ID NO 21
<211> LENGTH: 7
<212> TYPE: PRT
<213> ORGANISM: Artificial Sequence
<220> FEATURE:
<223> OTHER INFORMATION: Synthetic variable region sequence

<400> SEQUENCE: 21

Arg Ala Ser Asn Leu Glu Ser
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic variable region sequence

<400> SEQUENCE: 22

Gln Gln Ser Asn Lys Asp Pro Phe
1               5

<210> SEQ ID NO 23
<211> LENGTH: 10
<212> TYPE: PRT
<213> ORGANISM: Artificial Sequence
<220> FEATURE:
<223> OTHER INFORMATION: Synthetic variable region sequence

<400> SEQUENCE: 23

Gly Phe Thr Phe Ser Thr Tyr Ala Met Asn
1               5                   10

<210> SEQ ID NO 24
<211> LENGTH: 19
<212> TYPE: PRT
<213> ORGANISM: Artificial Sequence
<220> FEATURE:
<223> OTHER INFORMATION: Synthetic variable region sequence

<400> SEQUENCE: 24

Arg Ile Arg Ser Glu Ser Tyr Asp Phe Ala Thr Phe Tyr Ala Asp Ser
1               5                   10                  15

Val Lys Asp

<210> SEQ ID NO 25
<211> LENGTH: 5
<212> TYPE: PRT
<213> ORGANISM: Artificial Sequence
<220> FEATURE:
<223> OTHER INFORMATION: Synthetic variable region sequence
```

<400> SEQUENCE: 25

Gly Gly Phe Asp Cys
1               5

<210> SEQ ID NO 26
<211> LENGTH: 151
<212> TYPE: PRT
<213> ORGANISM: Artificial Sequence
<220> FEATURE:
<223> OTHER INFORMATION: Synthetic variable region sequence

<400> SEQUENCE: 26

Glu Phe Met Glu Thr Asp Thr Leu Leu Leu Trp Val Leu Leu Leu Trp
1               5                   10                  15

Val Pro Gly Ser Thr Gly Asp Ile Val Leu Thr Gln Ser Pro Ala Ser
            20                  25                  30

Leu Ala Val Ser Leu Gly Gln Arg Ala Thr Ile Ser Cys Arg Ala Ser
        35                  40                  45

Glu Ser Val Asp Phe Tyr Gly Asn Arg Leu Leu His Trp Tyr Gln Gln
    50                  55                  60

Lys Pro Gly Gln Pro Pro Lys Leu Leu Ile Tyr Arg Ala Ser Asn Leu
65                  70                  75                  80

Glu Ser Gly Phe Pro Thr Arg Phe Ser Gly Ser Gly Ser Thr Thr Asp
                85                  90                  95

Phe Thr Leu Thr Ile Asp Pro Val Glu Ala Asp Val Ala Ser Tyr
            100                 105                 110

Tyr Cys Gln Gln Ser Asn Lys Asp Pro Phe Thr Phe Gly Gly Gly Thr
        115                 120                 125

Lys Leu Glu Ile Lys Arg Ala Asp Ala Ala Pro Thr Val Ser Ile Phe
    130                 135                 140

Pro Pro Ser Ser Lys Leu Gly
145                 150

<210> SEQ ID NO 27
<211> LENGTH: 153
<212> TYPE: PRT
<213> ORGANISM: Artificial Sequence
<220> FEATURE:
<223> OTHER INFORMATION: Synthetic variable region sequence

<400> SEQUENCE: 27

Glu Phe Met Asn Leu Trp Phe Asn Trp Ile Phe Phe Val Val Phe Tyr
1               5                   10                  15

Gln Gly Val Leu Cys Glu Val Gln Leu Val Glu Ser Gly Gly Glu Leu
            20                  25                  30

Val Gln Pro Lys Gly Ser Leu Lys Leu Ser Cys Ser Ala Ser Gly Phe
        35                  40                  45

Thr Phe Ser Thr Tyr Ala Met Asn Trp Phe Arg Gln Ala Pro Gly Lys
    50                  55                  60

Gly Leu Glu Trp Val Ala Arg Ile Arg Ser Glu Ser Tyr Asp Phe Ala
65                  70                  75                  80

Thr Phe Tyr Ala Asp Ser Val Lys Asp Arg Phe Thr Ile Ser Arg Asp
                85                  90                  95

Asp Ser Gln Ser Met Leu Tyr Leu Gln Met Asn Asn Leu Lys Thr Glu
            100                 105                 110

Asp Thr Ala Met Tyr Tyr Cys Val Arg Gly Gly Phe Asp Cys Trp Gly
        115                 120                 125

```
Gln Gly Thr Leu Val Thr Val Ser Pro Ala Lys Thr Thr Pro Pro Ser
    130                 135                 140

Val Tyr Pro Leu Val Pro Gly Ser Leu
145                 150

<210> SEQ ID NO 28
<211> LENGTH: 15
<212> TYPE: PRT
<213> ORGANISM: Artificial Sequence
<220> FEATURE:
<223> OTHER INFORMATION: Synthetic variable region sequence

<400> SEQUENCE: 28

Arg Ala Ser Glu Ser Val Asp Ser Tyr Gly Asn Ser Phe Met His
1               5                   10                  15

<210> SEQ ID NO 29
<211> LENGTH: 7
<212> TYPE: PRT
<213> ORGANISM: Artificial Sequence
<220> FEATURE:
<223> OTHER INFORMATION: Synthetic variable region sequence

<400> SEQUENCE: 29

Leu Ala Ser Asn Leu Glu Ser
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic variable region sequence

<400> SEQUENCE: 30

Gln Gln Asn Asn Glu Asp Pro Phe Thr
1               5

<210> SEQ ID NO 31
<211> LENGTH: 10
<212> TYPE: PRT
<213> ORGANISM: Artificial Sequence
<220> FEATURE:
<223> OTHER INFORMATION: Synthetic variable region sequence

<400> SEQUENCE: 31

Gly Phe Asn Ile Glu Asp Thr Phe Ile His
1               5                   10

<210> SEQ ID NO 32
<211> LENGTH: 17
<212> TYPE: PRT
<213> ORGANISM: Artificial Sequence
<220> FEATURE:
<223> OTHER INFORMATION: Synthetic variable region sequence

<400> SEQUENCE: 32

Arg Ile Asp Pro Ala Asn Gly Asn Thr Lys Tyr Asp Pro Lys Phe Gln
1               5                   10                  15

Gly

<210> SEQ ID NO 33
<211> LENGTH: 7
<212> TYPE: PRT
<213> ORGANISM: Artificial Sequence
```

```
<220> FEATURE:
<223> OTHER INFORMATION: Synthetic variable region sequence

<400> SEQUENCE: 33

Gly Arg Tyr Gly Val Ala Tyr
1               5

<210> SEQ ID NO 34
<211> LENGTH: 147
<212> TYPE: PRT
<213> ORGANISM: Artificial Sequence
<220> FEATURE:
<223> OTHER INFORMATION: Synthetic variable region sequence

<400> SEQUENCE: 34

Glu Phe Met Glu Thr Asp Thr Leu Leu Leu Trp Val Leu Leu Leu Trp
1               5                   10                  15

Val Pro Gly Ser Thr Gly Asn Ile Val Leu Thr Gln Ser Pro Ala Ser
                20                  25                  30

Leu Ala Val Ser Leu Gly Gln Arg Ala Thr Ile Ser Cys Arg Ala Ser
            35                  40                  45

Glu Ser Val Asp Ser Tyr Gly Asn Ser Phe Met His Trp Tyr Gln Gln
        50                  55                  60

Lys Pro Gly Gln Pro Pro Lys Leu Leu Ile Tyr Leu Ala Ser Asn Leu
65                  70                  75                  80

Glu Ser Gly Val Pro Val Arg Phe Ser Gly Ser Gly Ser Arg Thr Asp
                85                  90                  95

Phe Thr Leu Thr Ile Asp Pro Val Glu Ala Asp Asp Ala Ala Thr Tyr
            100                 105                 110

Tyr Cys Gln Gln Asn Asn Glu Asp Pro Phe Thr Phe Gly Ser Gly Thr
        115                 120                 125

Lys Leu Glu Ile Lys Arg Ala Asp Ala Ala Pro Thr Val Ser Ile Phe
    130                 135                 140

His Ile Gln
145

<210> SEQ ID NO 35
<211> LENGTH: 153
<212> TYPE: PRT
<213> ORGANISM: Artificial Sequence
<220> FEATURE:
<223> OTHER INFORMATION: Synthetic variable region sequence

<400> SEQUENCE: 35

Glu Phe Met Lys Trp Ser Trp Val Phe Leu Phe Leu Met Ala Val Val
1               5                   10                  15

Thr Gly Val Asn Ser Glu Leu Gln Leu Gln Gln Ser Gly Ala Glu Leu
                20                  25                  30

Val Lys Pro Gly Ala Ser Val Lys Leu Ser Cys Thr Ala Ser Gly Phe
            35                  40                  45

Asn Ile Glu Asp Thr Phe Ile His Trp Val Lys Gln Arg Pro Glu Gln
        50                  55                  60

Gly Leu Glu Trp Ile Gly Arg Ile Asp Pro Ala Asn Gly Asn Thr Lys
65                  70                  75                  80

Tyr Asp Pro Lys Phe Gln Gly Lys Ala Thr Ile Thr Ala Asp Thr Ser
                85                  90                  95

Ser Asn Thr Ala Tyr Leu Gln Leu Ser Ser Leu Thr Ser Glu Asp Thr
            100                 105                 110
```

-continued

```
Ala Val Tyr Tyr Cys Glu Glu Gly Arg Tyr Gly Val Ala Tyr Trp Gly
            115                 120                 125

Gln Gly Thr Leu Val Thr Val Ser Ala Ala Lys Thr Thr Pro Pro Ser
        130                 135                 140

Val Tyr Pro Leu Ala Pro Gly Ser Leu
145                 150

<210> SEQ ID NO 36
<211> LENGTH: 15
<212> TYPE: PRT
<213> ORGANISM: Artificial Sequence
<220> FEATURE:
<223> OTHER INFORMATION: Synthetic variable region sequence

<400> SEQUENCE: 36

Lys Ala Ser Gln Ser Val Asp Tyr Asp Gly Asp Ser Tyr Met Asn
1               5                   10                  15

<210> SEQ ID NO 37
<211> LENGTH: 7
<212> TYPE: PRT
<213> ORGANISM: Artificial Sequence
<220> FEATURE:
<223> OTHER INFORMATION: Synthetic variable region sequence

<400> SEQUENCE: 37

Ala Ala Ser Asn Leu Glu Ser
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic variable region sequence

<400> SEQUENCE: 38

Gln Gln Ser His Glu Asp Pro Leu Thr
1               5

<210> SEQ ID NO 39
<211> LENGTH: 10
<212> TYPE: PRT
<213> ORGANISM: Artificial Sequence
<220> FEATURE:
<223> OTHER INFORMATION: Synthetic variable region sequence

<400> SEQUENCE: 39

Gly Tyr Thr Phe Thr Asp Tyr Ser Met His
1               5                   10

<210> SEQ ID NO 40
<211> LENGTH: 17
<212> TYPE: PRT
<213> ORGANISM: Artificial Sequence
<220> FEATURE:
<223> OTHER INFORMATION: Synthetic variable region sequence

<400> SEQUENCE: 40

Trp Ile Asn Thr Glu Thr Gly Glu Pro Thr Tyr Ala Asp Asp Phe Lys
1               5                   10                  15

Gly

<210> SEQ ID NO 41
<211> LENGTH: 12
```

```
<212> TYPE: PRT
<213> ORGANISM: Artificial Sequence
<220> FEATURE:
<223> OTHER INFORMATION: Synthetic variable region sequence

<400> SEQUENCE: 41

Gly Gly Val Tyr Arg Tyr Asp Glu Gly Phe Ala Tyr
1               5                   10

<210> SEQ ID NO 42
<211> LENGTH: 151
<212> TYPE: PRT
<213> ORGANISM: Artificial Sequence
<220> FEATURE:
<223> OTHER INFORMATION: Synthetic variable region sequence

<400> SEQUENCE: 42

Val Asp Met Val Leu Ile Leu Leu Leu Trp Val Leu Leu Leu Trp
1               5                   10                  15

Val Pro Gly Ser Thr Gly Asp Ile Val Leu Thr Gln Ser Pro Ala Ser
                20                  25                  30

Leu Ala Val Ser Leu Gly Gln Arg Ala Thr Ile Ser Cys Lys Ala Ser
            35                  40                  45

Gln Ser Val Asp Tyr Asp Gly Asp Ser Tyr Met Asn Trp Tyr Gln Gln
    50                  55                  60

Lys Pro Gly Gln Pro Pro Lys Leu Leu Ile Tyr Ala Ala Ser Asn Leu
65                  70                  75                  80

Glu Ser Gly Ile Pro Ala Thr Phe Ser Gly Ser Gly Ser Gly Thr Asp
                85                  90                  95

Phe Thr Leu Asn Ile His Pro Val Glu Glu Glu Asp Ala Ala Thr Tyr
            100                 105                 110

Tyr Cys Gln Gln Ser His Glu Asp Pro Leu Thr Phe Gly Ala Gly Thr
        115                 120                 125

Lys Leu Glu Leu Lys Arg Ala Asp Ala Ala Pro Thr Val Ser Ile Phe
    130                 135                 140

Pro Pro Ser Ser Lys Leu Gly
145                 150

<210> SEQ ID NO 43
<211> LENGTH: 159
<212> TYPE: PRT
<213> ORGANISM: Artificial Sequence
<220> FEATURE:
<223> OTHER INFORMATION: Synthetic variable region sequence

<400> SEQUENCE: 43

Leu Val Asp Met Ala Trp Val Trp Thr Leu Leu Phe Leu Met Ala Ala
1               5                   10                  15

Ala Gln Ser Ile Gln Ala Gln Ile Gln Leu Val Gln Ser Gly Pro Glu
                20                  25                  30

Leu Lys Lys Pro Gly Glu Thr Val Lys Ile Ser Cys Lys Gly Ser Gly
            35                  40                  45

Tyr Thr Phe Thr Asp Tyr Ser Met His Trp Val Lys Gln Ala Pro Gly
    50                  55                  60

Lys Gly Leu Lys Trp Met Gly Trp Ile Asn Thr Glu Thr Gly Glu Pro
65                  70                  75                  80

Thr Tyr Ala Asp Asp Phe Lys Gly Arg Phe Ala Phe Ser Leu Glu Thr
                85                  90                  95

Ser Ala Ser Thr Ala Tyr Leu Gln Ile Asn Asn Leu Lys Asn Glu Asp
```

|  | 100 | 105 | 110 |
|---|---|---|---|

Thr Ala Thr Tyr Phe Cys Ala Arg Gly Gly Val Tyr Arg Tyr Asp Glu
    115                  120                125

Gly Phe Ala Tyr Trp Gly Gln Gly Thr Leu Val Ser Val Ser Ala Ala
    130                  135                140

Lys Thr Thr Pro Pro Val Tyr Pro Leu Val Pro Gly Ser Leu
145              150              155

<210> SEQ ID NO 44
<211> LENGTH: 36
<212> TYPE: DNA
<213> ORGANISM: Artificial Sequence
<220> FEATURE:
<223> OTHER INFORMATION: Synthetic primer

<400> SEQUENCE: 44
catatggcgt ccgtggccac tgaactgcgc tgccag                              36

<210> SEQ ID NO 45
<211> LENGTH: 35
<212> TYPE: DNA
<213> ORGANISM: Artificial Sequence
<220> FEATURE:
<223> OTHER INFORMATION: Synthetic primer

<400> SEQUENCE: 45
ggatccaagc ttttagttgg atttgtcact gttca                                 35